US009704216B1

(12) United States Patent
Laskar et al.

(10) Patent No.: US 9,704,216 B1
(45) Date of Patent: Jul. 11, 2017

(54) DYNAMIC SIZE ADJUSTMENT OF RENDERED INFORMATION ON A DISPLAY SCREEN

(71) Applicant: Le Technology, Inc., San Jose, CA (US)

(72) Inventors: Supratim Laskar, San Diego, CA (US); Kyong Kim, San Diego, CA (US)

(73) Assignee: Le Technology, San Jose, CA (US)

( * ) Notice: Subject to any disclaimer, the term of this patent is extended or adjusted under 35 U.S.C. 154(b) by 0 days.

(21) Appl. No.: 15/228,963

(22) Filed: Aug. 4, 2016

(51) Int. Cl.
*G06F 3/01* (2006.01)
*G06T 3/40* (2006.01)
*A61B 3/00* (2006.01)

(52) U.S. Cl.
CPC .............. *G06T 3/40* (2013.01); *A61B 3/0025* (2013.01); *G06F 3/012* (2013.01); *G06F 3/013* (2013.01)

(58) Field of Classification Search
None
See application file for complete search history.

(56) References Cited

U.S. PATENT DOCUMENTS

| 8,515,491 | B2* | 8/2013 | Das | H04M 1/72569 |
| | | | | 455/557 |
| 8,913,005 | B2* | 12/2014 | Uppuluri | G06K 9/00221 |
| | | | | 345/156 |
| 8,957,847 | B1* | 2/2015 | Karakotsios | G06F 3/013 |
| | | | | 345/156 |
| 2009/0292988 | A1 | 11/2009 | Weng | |
| 2010/0188426 | A1* | 7/2010 | Ohmori | G06F 3/012 |
| | | | | 345/660 |
| 2010/0303294 | A1* | 12/2010 | Zschau | A61B 3/113 |
| | | | | 382/103 |

(Continued)

OTHER PUBLICATIONS

Øygard, Audun M. "Head Tracking with Web RTC" downloaded Jun. 23, 2016 from http://auduno.com/post/25125149521/head-tracking-with-webrtc, 6 pages.

(Continued)

*Primary Examiner* — Ryan M Gray
(74) *Attorney, Agent, or Firm* — Rutan & Tucker LLP

(57) ABSTRACT

Provided herein in some embodiments is an apparatus including a rendered information-adjustment module configured to cooperate with a display interface to dynamically size-adjust rendered information displayed on the display screen, a distance module, a vision properties module, and a display modification module. The distance module can be configured to periodically determine a facial proximity to the display screen for the user in accordance with a periodic algorithm. The vision properties module can be configured to collect vision properties and store the vision properties in a vision record for the user. The display modification module can be configured to determine a direction and a magnitude for adjusting the rendered information to a new size. The periodic algorithm conserves the battery power by periodically invoking the one or more facial proximity sensors, which, in turn, reduces otherwise continuous battery power-draining size adjustments to the rendered information on the display screen.

20 Claims, 11 Drawing Sheets

(not to scale)

(56) References Cited

U.S. PATENT DOCUMENTS

Figure 4:
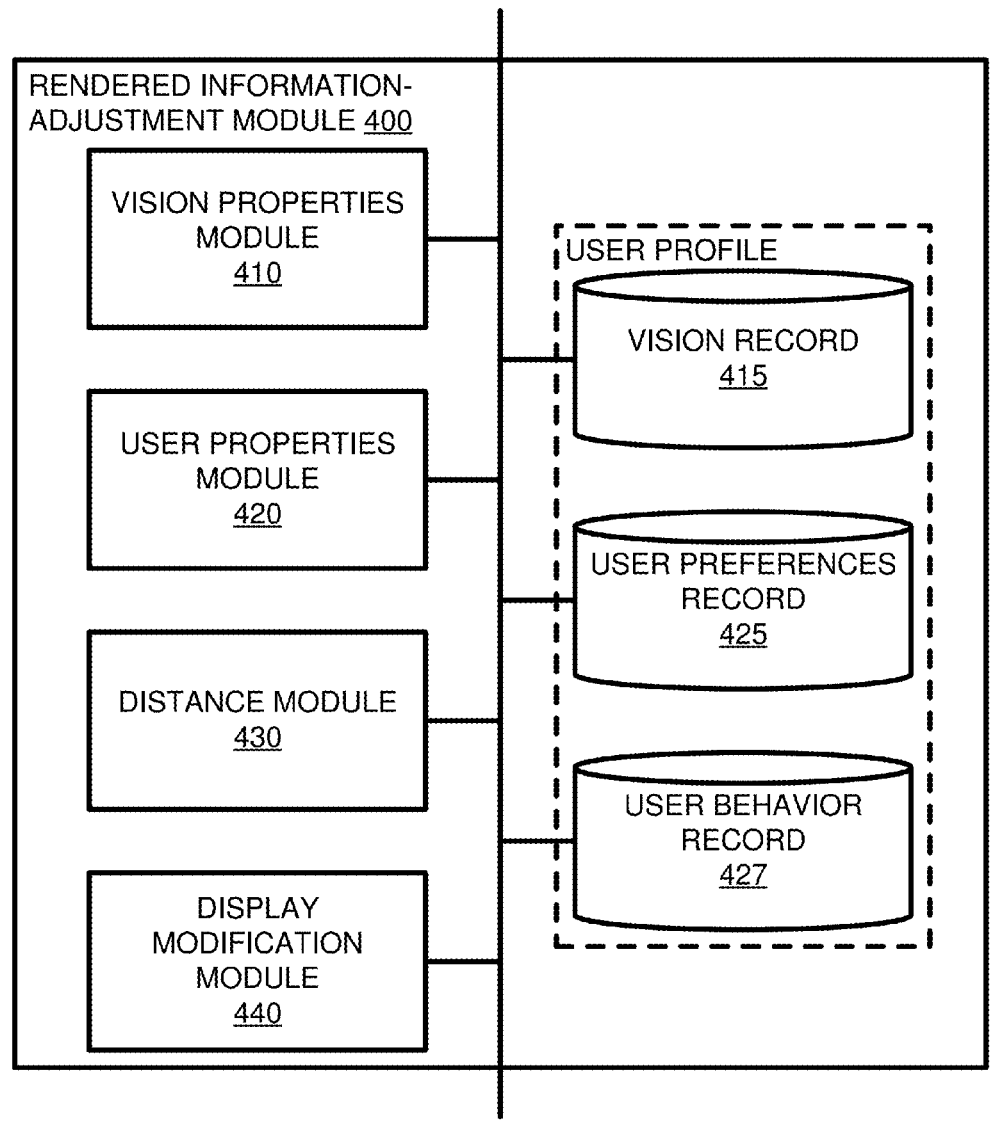

| | | | |
|---|---|---|---|
| 2011/0084897 A1* | 4/2011 | Manoharan | G06F 1/1626 |
| | | | 345/156 |
| 2012/0038546 A1* | 2/2012 | Cromer | G06F 1/1626 |
| | | | 345/156 |
| 2012/0218398 A1 | 8/2012 | Mehra | |
| 2012/0243735 A1* | 9/2012 | Wu | G09G 5/30 |
| | | | 382/103 |
| 2013/0057553 A1 | 3/2013 | Chakravarthula et al. | |
| 2013/0057573 A1* | 3/2013 | Chakravarthula | G06F 3/005 |
| | | | 345/619 |
| 2014/0118257 A1 | 5/2014 | Baldwin | |
| 2014/0137054 A1* | 5/2014 | Gandhi | G06F 3/013 |
| | | | 715/865 |
| 2014/0168274 A1 | 6/2014 | Wang et al. | |
| 2015/0242993 A1* | 8/2015 | Raman | G01V 8/12 |
| | | | 345/589 |

OTHER PUBLICATIONS

Bonsor, Kevin and Johnson, Ryan "How Facial Recognition Systems Work", 11 pages Copyright 2016 HowStuffWorks, a division of InfoSpace LLC.

"Headtrackr" downloaded Jun. 23, 2016 from GitHub—auduno/headtrackr: Javascript library for headtracking via webcam and WebRTC/getUserMe . . . , 3 pages.

Limer, Eric, "You'll Never Squint Again with This Automatically Resizing Font", downloaded Jun. 23, 2016 from http://gizmodo.com/5983358/youll-never-squint-again-with-this-automatically-resizing-font , 2 pages. Feb. 11, 2013 Gizmodo.

* cited by examiner

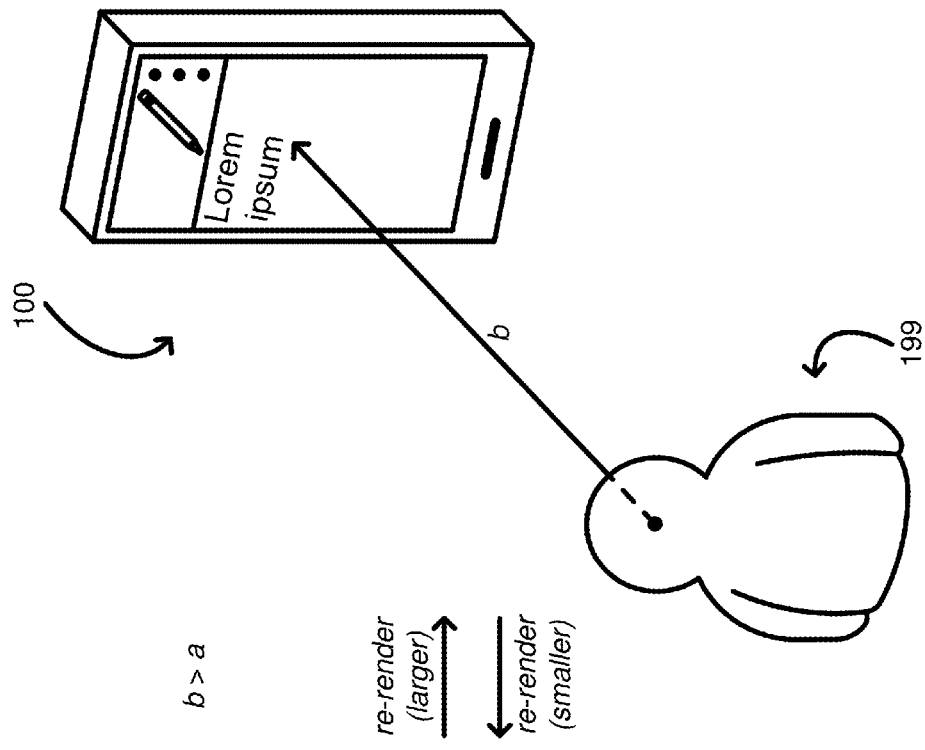
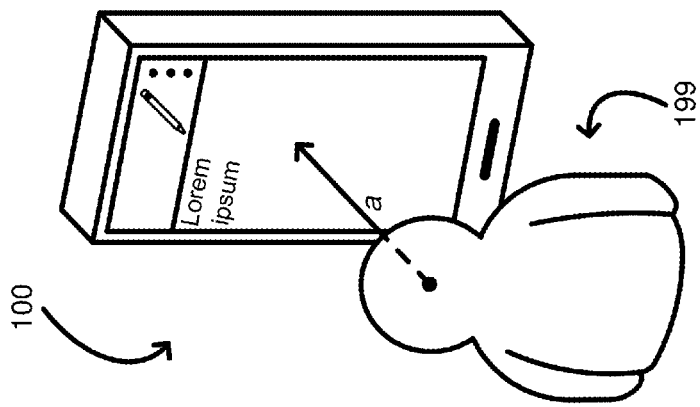
FIG. 1B
FIG. 1A

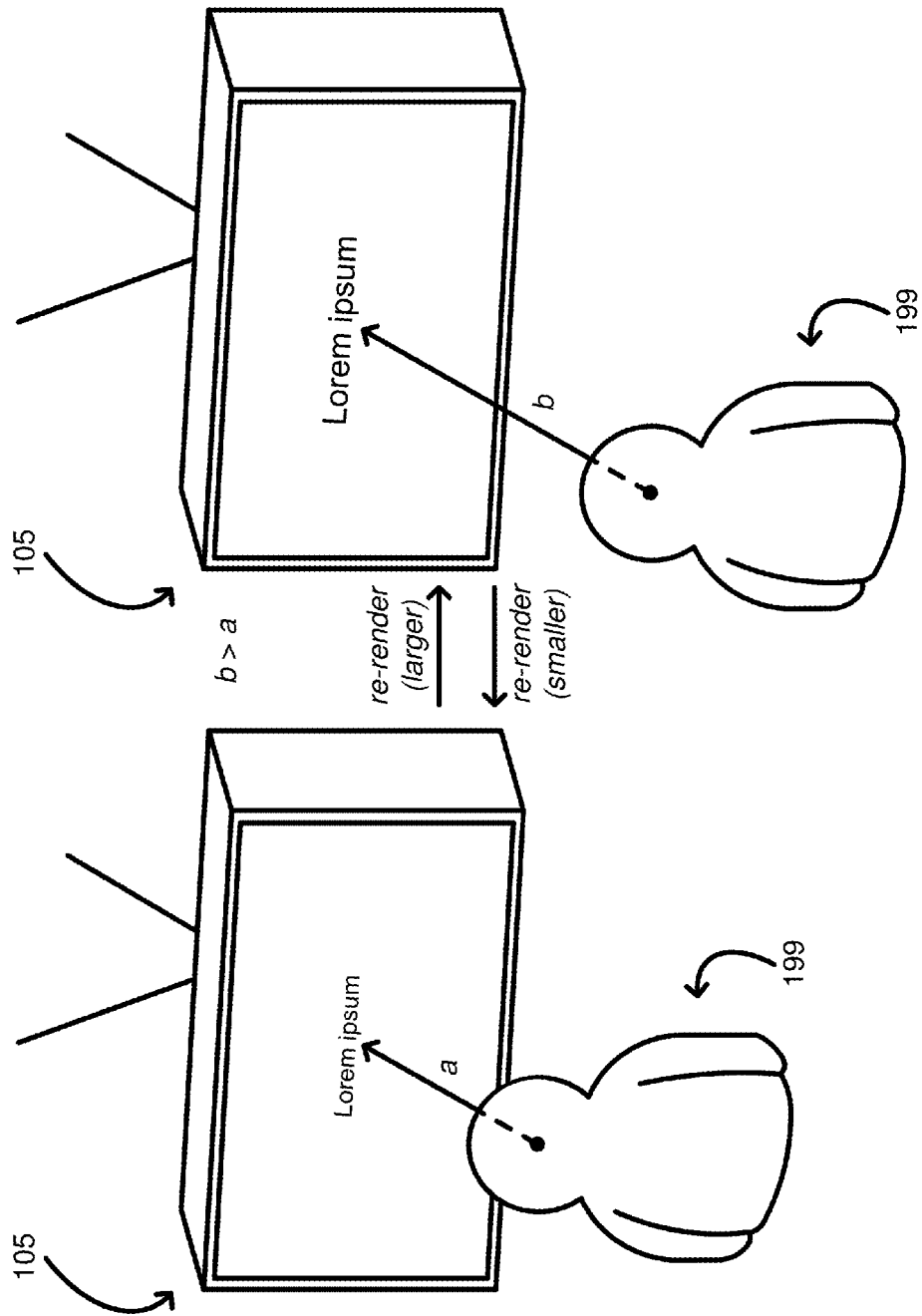

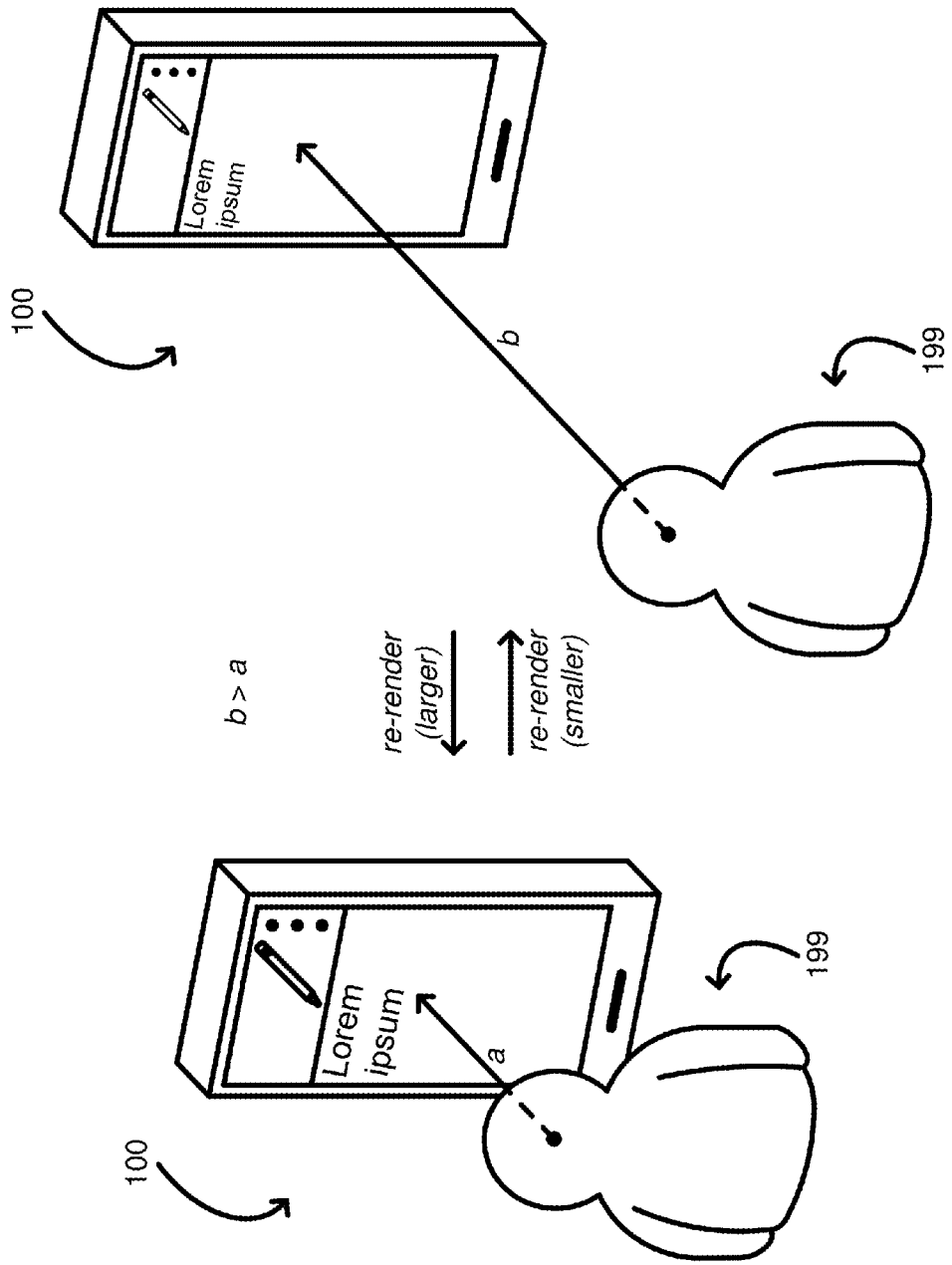

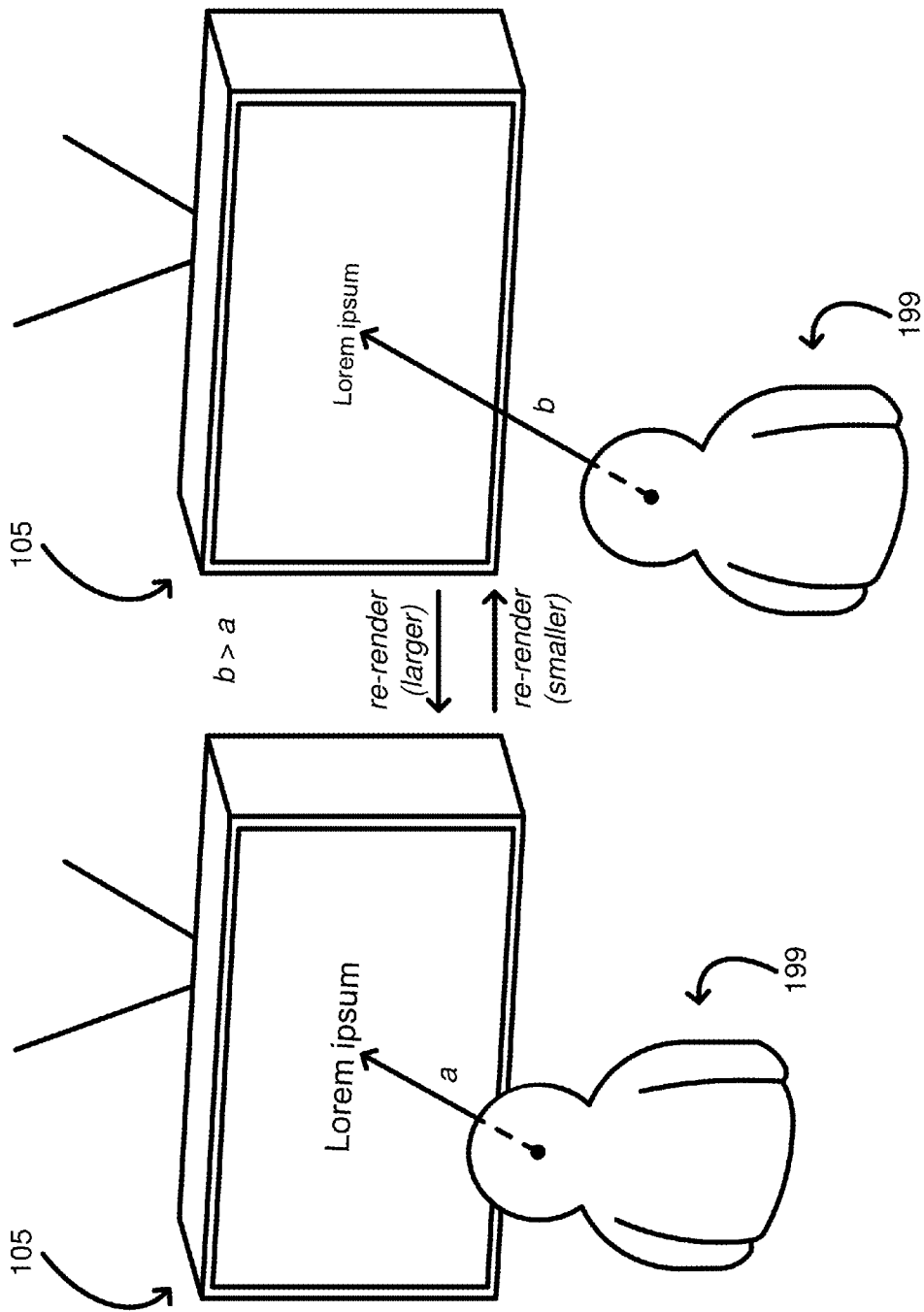

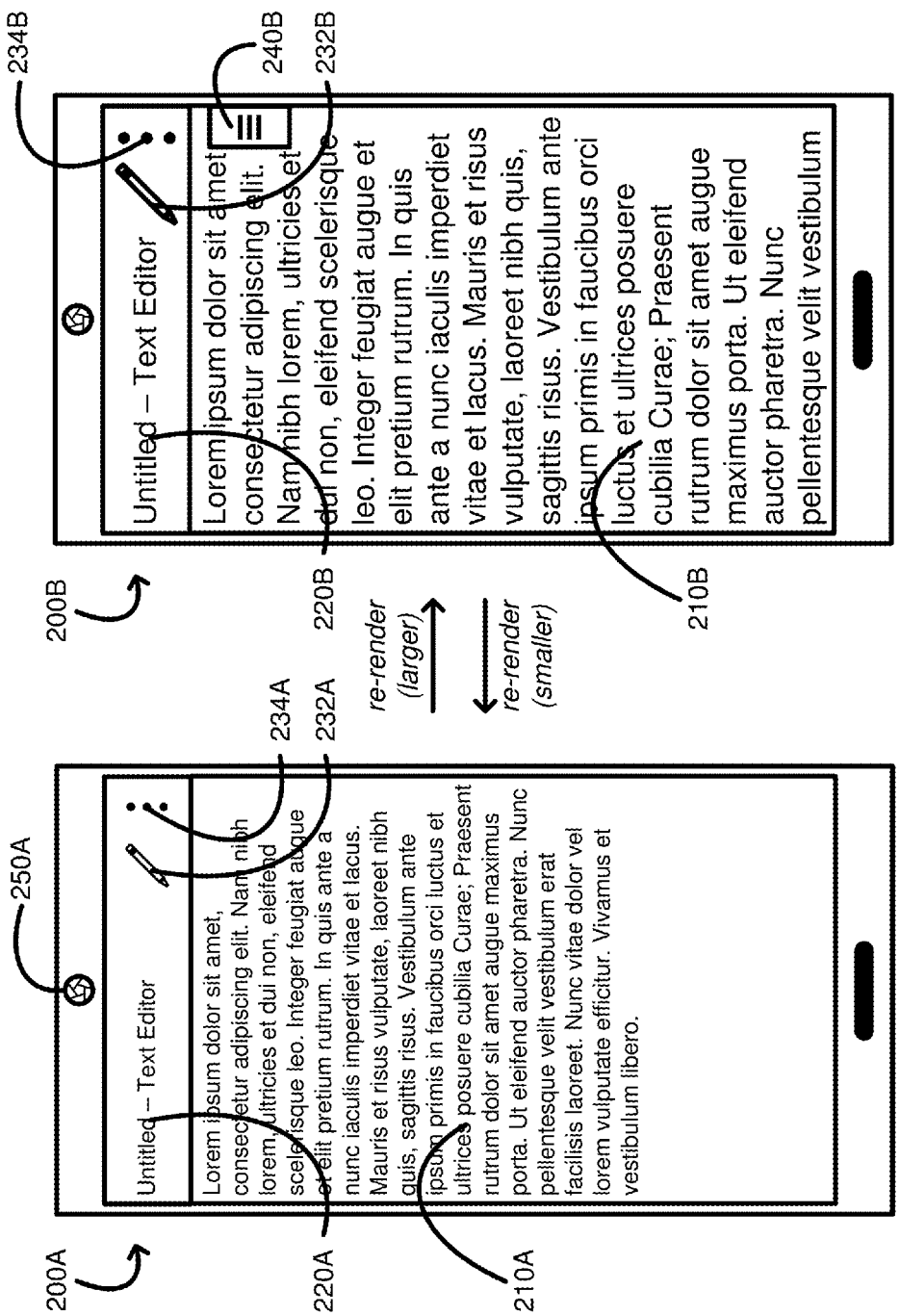

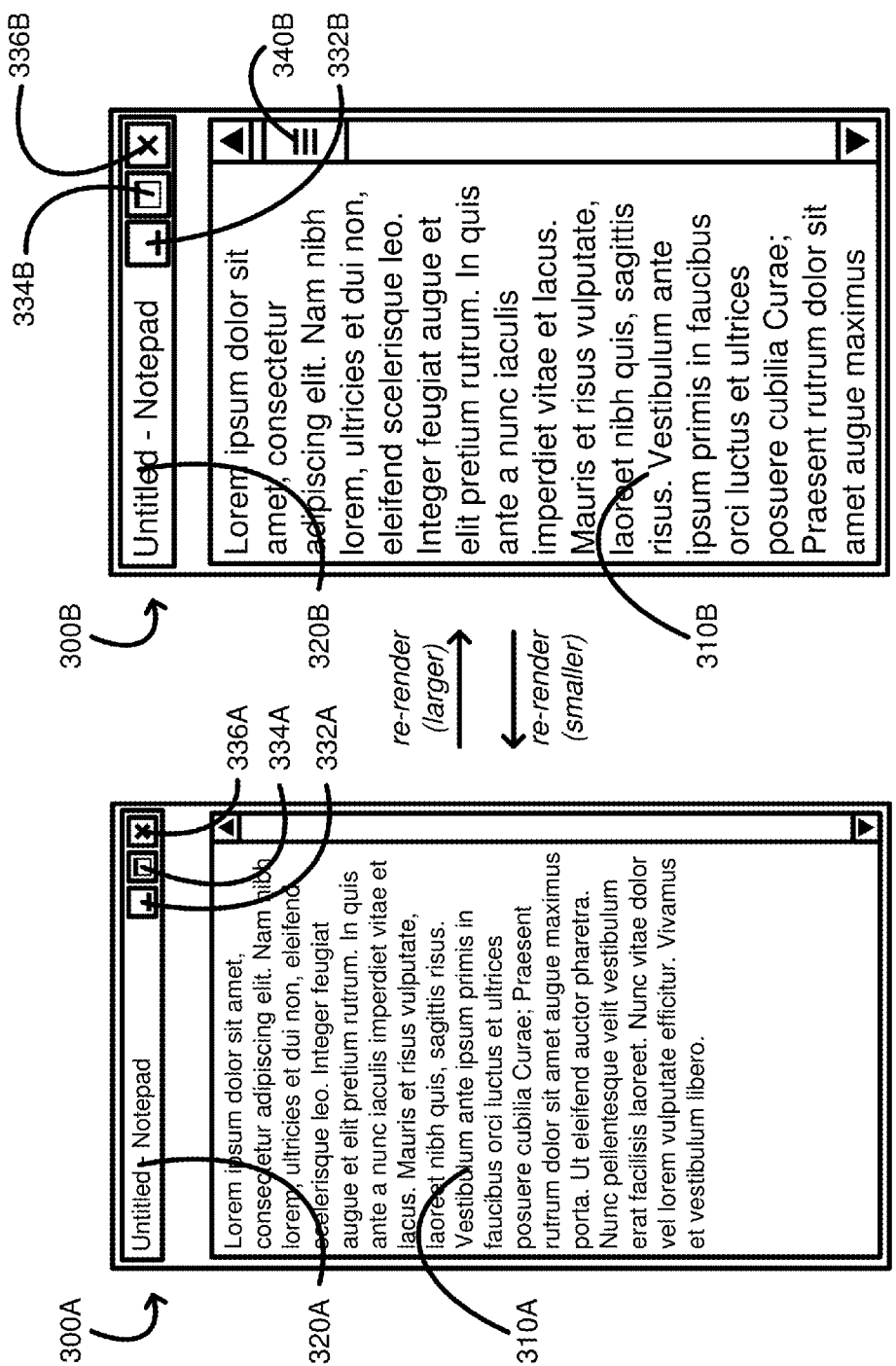

DYNAMIC SIZE ADJUSTMENT OF RENDERED INFORMATION ON A DISPLAY SCREEN

NOTICE OF COPYRIGHT

A portion of the disclosure of this patent application contains material that is subject to copyright protection. The copyright owner has no objection to the facsimile reproduction by anyone of the software engine and its modules, as it appears in the United States Patent & Trademark Office's patent file or records, but otherwise reserves all copyright rights whatsoever.

FIELD

Embodiments of the design provided herein generally relate to dynamically resizing rendered information on a display screen in accordance with a user's distance from the display screen, the user's vision, or a combination thereof.

BACKGROUND

Rendered text and images displayed on a display screen of an electronic device such as a mobile phone, a personal computer, or a television might not be suitably sized for all users of the electronic device because each user might be most comfortable viewing or most clearly see the rendered text and images at a different distance from the display screen. Furthermore, each user's vision might be clinically different, which can directly affect the distance from a display screen that is best in terms of comfort and clarity for a user when viewing rendered text and images on the display screen. For example, a user might have myopia (nearsightedness), and the user might need to view the rendered text and images at a distance relatively close to the display screen. For example, a user might have hyperopia (farsightedness), and the user might need to view the rendered text and images at a distance relatively far from the display screen. Provided herein are systems and methods that address the foregoing by dynamically resizing rendered information on a display screen in accordance with a user's distance from the display screen, the user's vision, or a combination thereof.

SUMMARY

Provided herein in some embodiments is an apparatus including a rendered information-adjustment module of a mobile computing device, wherein the rendered information-adjustment module is configured to cooperate with components of the mobile computing device. The components of the mobile computing device can include one or more processors to execute instructions, one or more memories to store information, one or more data input components to receive data input from a user of the mobile computing device, a communication circuit to establish a communication link to communicate with other computing devices external to the mobile computing device, a display screen to display at least some of the information stored in the one or more memories, one or more facial proximity sensors configured to provide facial proximity data for the user, and a battery to provide battery power to the mobile computing device. Portions of the rendered information-adjustment module can be implemented in software stored in the one or more memories and executed by the one or more processors. The rendered information-adjustment module can be configured to cooperate with a display interface to dynamically size-adjust rendered information displayed on the display screen. The rendered information-adjustment module can be further configured to cooperate with a distance module, a vision properties module, and a display modification module. The distance module can be configured to periodically determine a facial proximity to the display screen for the user in accordance with a periodic algorithm. The vision properties module can be configured to collect vision properties and store the vision properties in a vision record for the user. The display modification module can be configured to determine a direction and a magnitude for adjusting the rendered information to a new size. The periodic algorithm conserves the battery power by periodically invoking the one or more facial proximity sensors, which, in turn, reduces otherwise continuous battery power-draining size adjustments to the rendered information on the display screen.

Also provided herein in some embodiments is a method for the foregoing apparatus, including re-rendering the rendered information with the rendered information-adjustment module of the mobile computing device; periodically determining with the distance module the facial proximity to the display screen for the user in accordance with the periodic algorithm; collecting the vision properties with the vision properties module and storing the vision properties in the vision record for the user; determining with the display modification module the direction and the magnitude for adjusting the rendered information to a new size; and conserving the battery power by periodically invoking the one or more facial proximity sensors with the periodic algorithm, thereby reducing otherwise continuous battery power-draining size adjustments to the rendered information on the display screen.

These and other features of the design provided herein can be better understood with reference to the drawings, description, and claims, all of which form the disclosure of this patent application.

DRAWINGS

The drawings refer to some embodiments of the design provided herein in which:

FIGS. 1A and 1B provide a schematic illustrating dynamically resizing rendered information on a display screen of a mobile computing device in accordance with a user's distance from a display screen, the user's vision, or a combination thereof in accordance with some embodiments.

FIGS. 1C and 1D provide a schematic illustrating dynamically resizing rendered information on a display screen of a television in accordance with a user's distance from a display screen, the user's vision, or a combination thereof in accordance with some embodiments.

FIGS. 1E and 1F provide a schematic illustrating dynamically resizing rendered information on a display screen of a mobile computing device in accordance with a user's distance from a display screen, the user's vision, or a combination thereof in accordance with some embodiments.

FIGS. 1G and 1H provide a schematic illustrating dynamically resizing rendered information on a display screen of a television in accordance with a user's distance from a display screen, the user's vision, or a combination thereof in accordance with some embodiments.

FIGS. 2A and 2B provide a schematic illustrating dynamically resizing rendered information on a display screen of a mobile computing device in accordance with some embodiments.

FIGS. 3A and 3B provide a schematic illustrating dynamically resizing rendered information on a display screen of a personal computer in accordance with some embodiments.

FIG. 4 provides a schematic illustrating a rendered information-adjustment module 400 in accordance with some embodiments.

Figure 5:
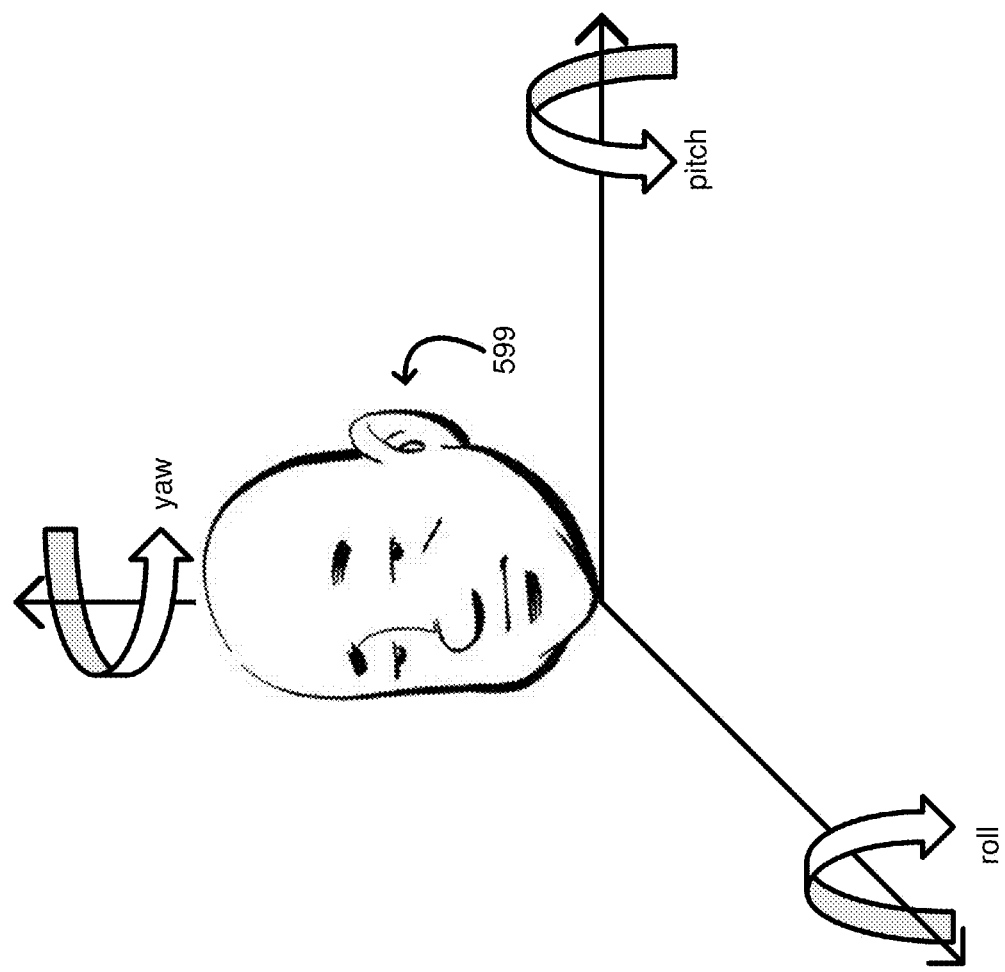

FIG. 5 provides a schematic illustrating user head motions accounted for by a rendered information-adjustment module in accordance with some embodiments.

Figure 6:
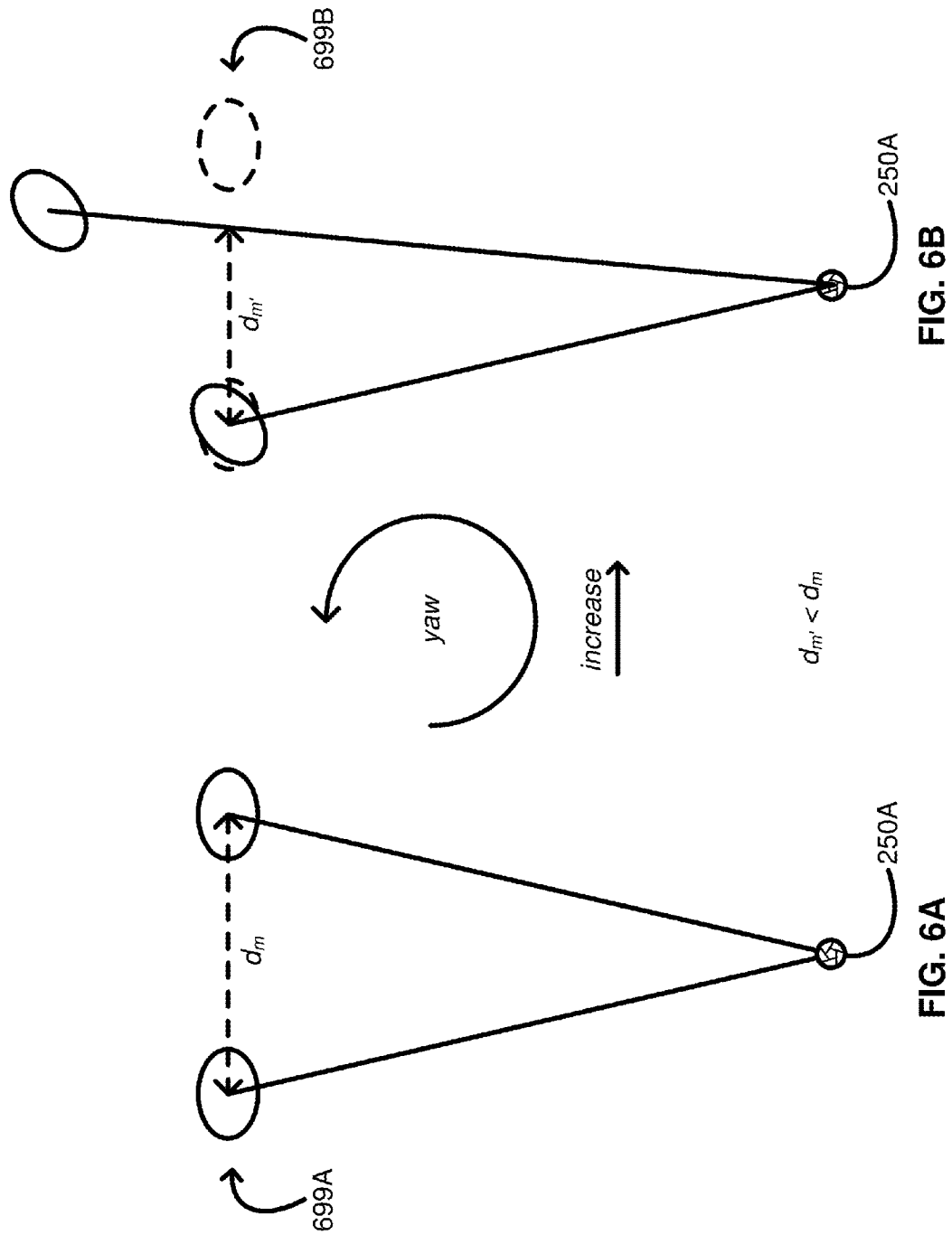

FIGS. 6A and 6B provide a schematic illustrating user head yaw and its effect on a raw measured inter-eye distance for the user in accordance with some embodiments.

Figure 7:
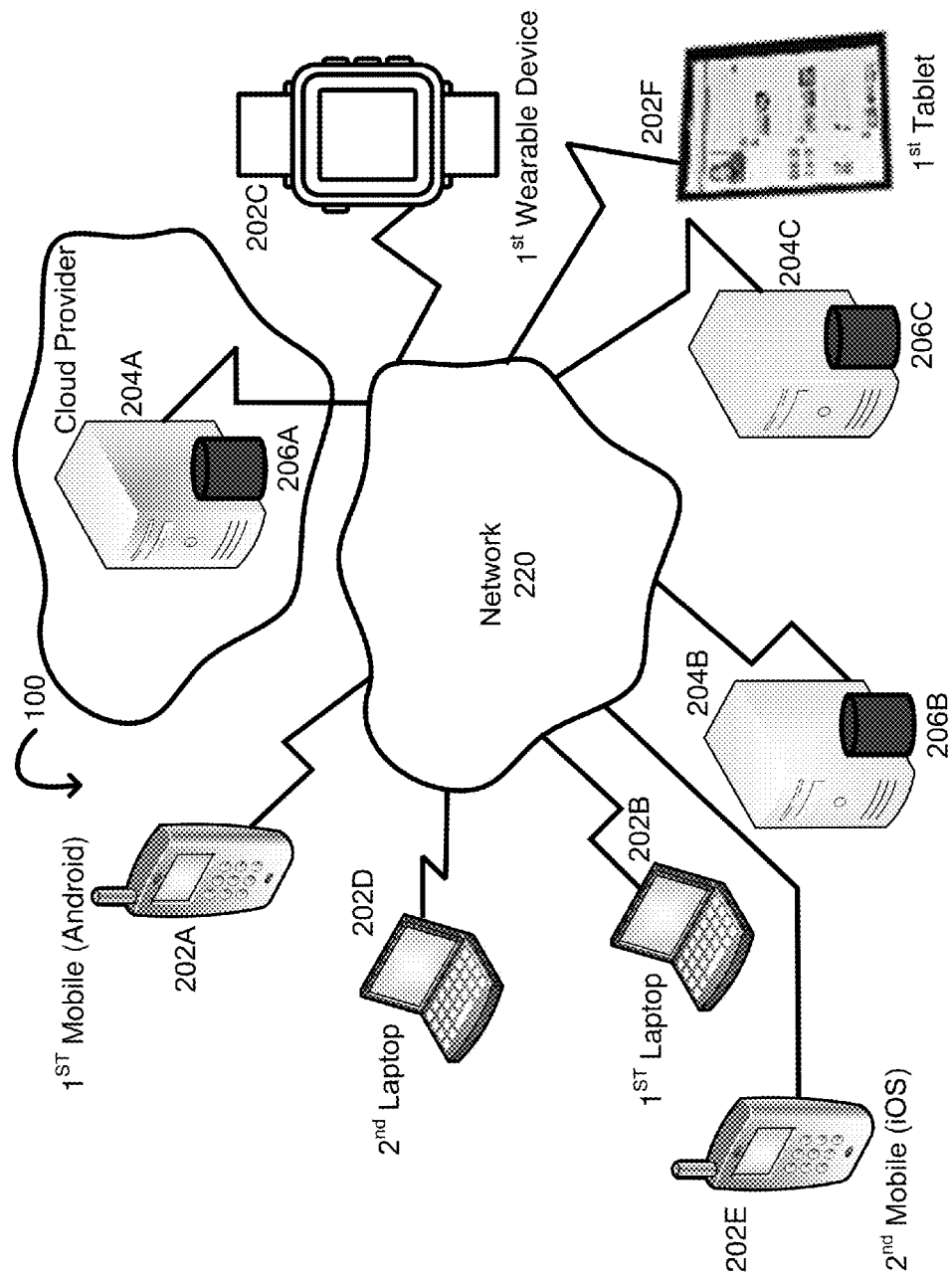

FIG. 7 provides one or more networks in accordance with some embodiments.

Figure 8:
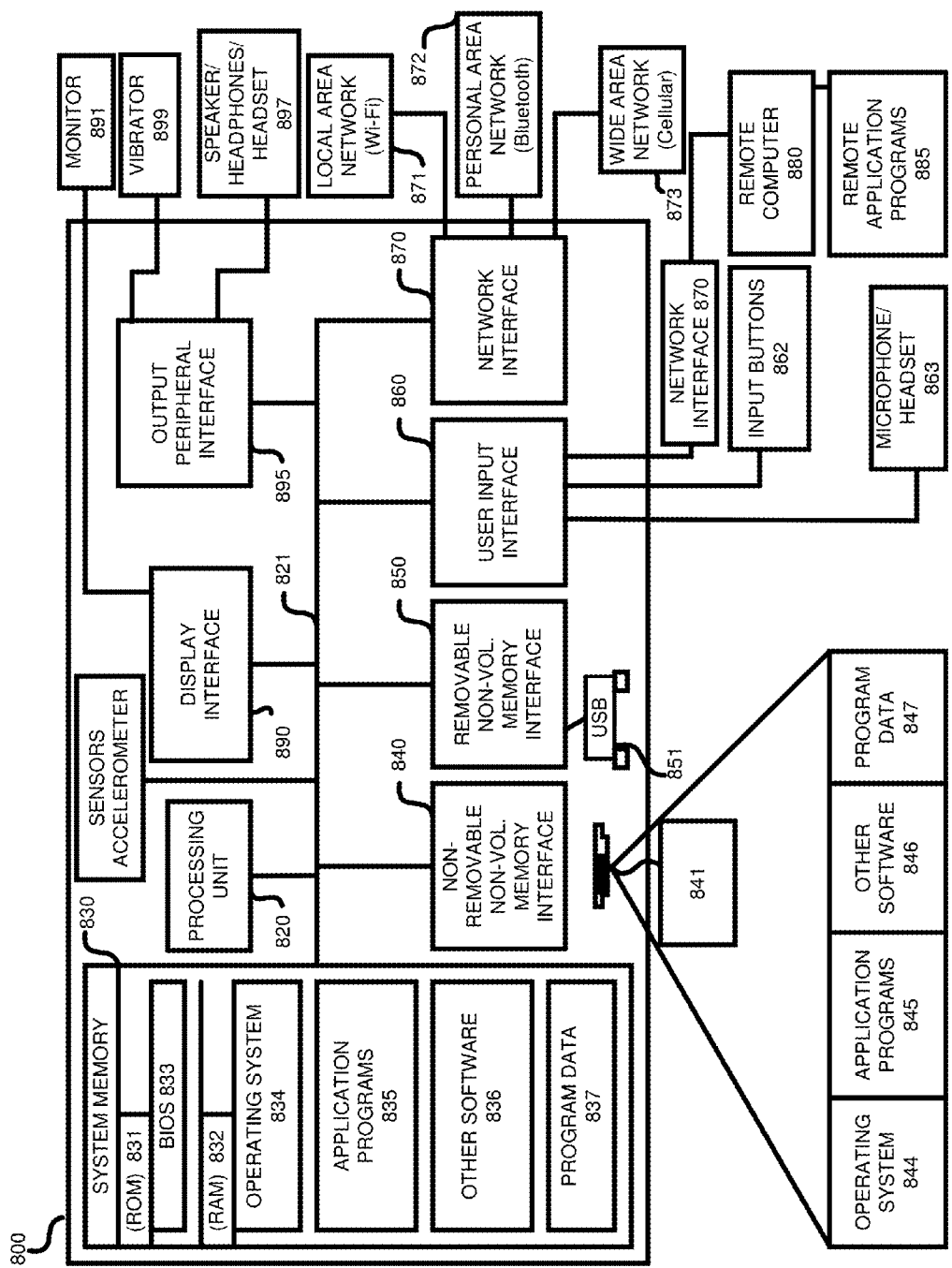

FIG. 8 provides one or more computing systems in accordance with some embodiments.

While the design is subject to various modifications, equivalents, and alternative forms, specific embodiments thereof have been shown by way of example in the drawings and will now be described in detail. It should be understood that the design is not limited to the particular embodiments disclosed, but—on the contrary—the intention is to cover all modifications, equivalents, and alternative forms using the specific embodiments.

DESCRIPTION

In the following description, numerous specific details are set forth, such as examples of specific data signals, named components, memory in a device, etc., in order to provide a thorough understanding of the present design. It will be apparent, however, to one of ordinary skill in the art that the present design can be practiced without these specific details. In other instances, well known components or methods have not been described in detail but rather in a block diagram in order to avoid unnecessarily obscuring the present design. Further, specific numeric references such as first driver, can be made. However, the specific numeric reference should not be interpreted as a literal sequential order but rather interpreted that the first notification is different than a second notification. Thus, the specific details set forth are merely exemplary. The specific details can be varied from and still be contemplated to be within the spirit and scope of the present design. The term coupled is defined as meaning connected either directly to the component or indirectly to the component through another component.

Unless defined otherwise, all technical and scientific terms used herein have the same meaning as commonly understood by persons of ordinary skill in the art. In an example, "rendering" includes generating text, user interface ("UI") elements, and the like into rendered information. In another example, "compositing" includes scaling and arranging the rendered information in a display space such as on a display screen.

Rendered text and images displayed on a display screen of an electronic device such as a mobile phone, a personal computer, or a television might not be suitably sized for all users of the electronic device because each user might be most comfortable viewing or most clearly see the rendered text and images at a different distance from the display screen. Furthermore, each user's vision might be clinically different, which can directly affect the distance from a display screen that is best in terms of comfort and clarity for a user when viewing rendered text and images on the display screen. For example, a user might have myopia (nearsightedness), and the user might need to view the rendered text and images at a distance relatively close to the display screen. For example, a user might have hyperopia (farsightedness), and the user might need to view the rendered text and images at a distance relatively far from the display screen. Provided herein are systems and methods that address the foregoing by dynamically resizing rendered information on a display screen in accordance with a user's distance from the display screen, the user's vision, or a combination thereof.

In some embodiments, for example, an apparatus is provided including a rendered information-adjustment module of a computing device such as a mobile computing device, wherein the rendered information-adjustment module is configured to cooperate with components of the computing device. The components of the computing device can include one or more processors to execute instructions, one or more memories to store information, one or more data input components to receive data input from a user of the computing device, a communication circuit to establish a communication link to communicate with other computing devices external to the computing device, a display screen to display at least some of the information stored in the one or more memories, one or more facial proximity sensors configured to provide facial proximity data for the user, and power source such as a battery to provide power to the computing device. Portions of the rendered information-adjustment module can be implemented in software stored in the one or more memories and executed by the one or more processors. The rendered information-adjustment module can be configured to cooperate with a display interface to dynamically size-adjust rendered information displayed on the display screen. The rendered information-adjustment module can be further configured to cooperate with a distance module, a vision properties module, and a display modification module. The distance module can be configured to periodically determine a facial proximity to the display screen for the user in accordance with a periodic algorithm. The vision properties module can be configured to collect vision properties and store the vision properties in a vision record for the user. The display modification module can be configured to determine a direction and a magnitude for adjusting the rendered information to a new size. The periodic algorithm conserves the battery power by periodically invoking the one or more facial proximity sensors, which, in turn, reduces otherwise continuous battery power-draining size adjustments to the rendered information on the display screen.

Also provided herein in some embodiments is a method for the foregoing apparatus, including re-rendering the rendered information with the rendered information-adjustment module of the computing device; periodically determining with the distance module the facial proximity to the display screen for the user in accordance with the periodic algorithm; collecting the vision properties with the vision properties module and storing the vision properties in the vision record for the user; determining with the display modification module the direction and the magnitude for adjusting the rendered information to a new size; and conserving the power by periodically invoking the one or more facial proximity sensors with the periodic algorithm, thereby reducing otherwise continuous power-draining size adjustments to the rendered information on the display screen.

FIGS. 1A and 1B provide a schematic illustrating dynamically resizing rendered information on a display screen of a mobile computing device in accordance with a user's distance from a display screen, the user's vision, or a combination thereof in accordance with some embodiments.

As shown in FIGS. 1A and 1B, a user 199 of a mobile computing device 100 can view rendered information such as rendered text and any UI elements such as iconography, icons, or the like on a display screen of the mobile computing device from a distance a (e.g., length of partially extended arm), a distance b (e.g., length of fully extended arm), or some distance between distances a and b. Beginning with FIG. 1A, should the user be more comfortable viewing or more clearly see the rendered text and UI elements at a farther distance from the display screen, the user can move the mobile computing device from the distance a to the distance b as shown in FIG. 1B to increase the size of the rendered information. Turning to FIG. 1B, should the user instead be more comfortable viewing or more clearly see the rendered text and UI elements at a closer distance to the display screen, the user can move the mobile computing device from the distance b to the distance a as shown in FIG. 1A to decrease the size of the rendered information. In accordance with systems and methods provided herein, moving the mobile computing device from the distance a to the distance b invokes a rendered information-adjustment module that dynamically resizes, and, thereby, re-renders the originally rendered information on the display screen such that the re-rendered information is larger than the originally rendered information. Likewise, moving the mobile computing device from the distance b to the distance a invokes the rendered information-adjustment module that dynamically resizes, and, thereby, re-renders the originally rendered information on the display screen such that the re-rendered information is smaller than the originally rendered information.

Additionally or alternatively, the systems and methods provided herein are configured to account for a myopic user of the mobile computing device. As described in further detail herein, a vision properties module can be configured to collect vision properties (e.g., myopia) associated with the myopic user and store the vision properties in a vision record for the myopic user. In cooperation with the vision properties module, the rendered information-adjustment module can account for the myopic user's myopia and dynamically resize the rendered information accordingly, for example, by using a myopic factor (e.g., >1) for dynamically resizing the rendered information. For example, the myopic factor can be used to effect re-rendered information that is larger at the distance b for the myopic user than for a user without myopia.

FIGS. 1C and 1D provide a schematic illustrating dynamically resizing rendered information on a display screen of a television in accordance with a user's distance from a display screen, the user's vision, or a combination thereof in accordance with some embodiments.

While FIGS. 1A and 1B are directed to a mobile computing device, it should be understood that systems provided herein also include electronic devices such as personal computers, televisions such as television 105, smart electronic systems on bicycles ("smart bicycles"), and smart electronic systems on automobiles ("smart automobiles"). As shown in FIGS. 1C and 1D, a user 199 can likewise view rendered information such as rendered text and any UI elements on a display screen of the television 105 from a distance a (e.g., length of a fully extended arm), a distance b (e.g., recommended viewing distance in accordance with a size of the television 105), or some distance between distances a and b. Beginning with FIG. 1C, should the user be more comfortable viewing or more clearly see the rendered text and UI elements at a farther distance from the display screen, the user can move from the distance a to the distance b as shown in FIG. 1D to increase the size of the rendered information. Turning to FIG. 1D, should the user instead be more comfortable viewing or more clearly see the rendered text and UI elements at a closer distance to the display screen, the user can move from the distance b to the distance a as shown in FIG. 1C to decrease the size of the rendered information. In accordance with systems and methods provided herein, moving from the distance a to the distance b invokes a rendered information-adjustment module that dynamically resizes, and, thereby, re-renders the originally rendered information on the display screen such that the re-rendered information is larger than the originally rendered information. Likewise, moving from the distance b to the distance a invokes the rendered information-adjustment module that dynamically resizes, and, thereby, re-renders the originally rendered information on the display screen such that the re-rendered information is smaller than the originally rendered information. Additionally or alternatively, the systems and methods provided herein are configured to account for a myopic user of the mobile computing device.

FIGS. 1E and 1F provide a schematic illustrating dynamically resizing rendered information on a display screen in accordance with a user's distance from a display screen, the user's vision, or a combination thereof in accordance with some embodiments.

As shown in FIGS. 1E and 1F, a user 199 of a mobile computing device 100 can view rendered information such as rendered text and UI elements on a display screen of the mobile computing device from a distance a (e.g., length of partially extended arm), a distance b (e.g., length of fully extended arm), or some distance between distances a and b. Beginning with FIG. 1F, should the user be more comfortable viewing or more clearly see the rendered text and UI elements at a closer distance to the display screen, the user can move the mobile computing device from the distance b to the distance a as shown in FIG. 1E to increase the size of the rendered information. Turning to FIG. 1E, should the user instead be more comfortable viewing or more clearly see the rendered text and UI elements at a farther distance from the display screen, the user can move the mobile computing device from the distance a to the distance b as shown in FIG. 1F to decrease the size of the rendered information. In accordance with systems and methods provided herein, moving the mobile computing device from the distance b to the distance a invokes a rendered information-adjustment module that dynamically resizes, and, thereby, re-renders the originally rendered information on the display screen such that the re-rendered information is larger than the originally rendered information. Likewise, moving the mobile computing device from the distance a to the distance b invokes the rendered information-adjustment module that dynamically resizes, and, thereby, re-renders the originally rendered information on the display screen such that the re-rendered information is smaller than the originally rendered information.

Additionally or alternatively, the systems and methods provided herein are configured to account for a hyperopic user of the mobile computing device. As described in further detail herein, a vision properties module can be configured to collect vision properties (e.g., hyperopia) associated with the hyperopic user and store the vision properties in a vision record for the hyperopic user. In cooperation with the vision properties module, the rendered information-adjustment module can account for the hyperopic user's hyperopia and dynamically resize the rendered information accordingly, for example, by using a hyperopic factor (e.g., <1) for dynamically resizing the rendered information. For example, the hyperopic factor can be used to effect re-rendered information that is smaller at the distance b for the hyperopic user than for a user without hyperopia.

FIGS. 1G and 1H provide a schematic illustrating dynamically resizing rendered information on a display screen of a television in accordance with a user's distance from a display screen, the user's vision, or a combination thereof in accordance with some embodiments.

While FIGS. 1E and 1F are directed to a mobile computing device, it should be understood that systems provided herein also include electronic devices such as personal computers, televisions such as television 105, smart bicycles, and smart automobiles. As shown in FIGS. 1G and 1H, a user 199 can likewise view rendered information such as rendered text and UI elements on a display screen of the television 105 from a distance a (e.g., length of a fully extended arm), a distance b (e.g., recommended viewing distance in accordance with a size of the television 105), or some distance between distances a and b. Beginning with FIG. 1H, should the user be more comfortable viewing or more clearly see the rendered text and UI elements at a closer distance to the display screen, the user can move from the distance b to the distance a as shown in FIG. 1G to increase the size of the rendered information. Turning to FIG. 1G, should the user instead be more comfortable viewing or more clearly see the rendered text and UI elements at a farther distance from the display screen, the user can move from the distance a to the distance b as shown in FIG. 1H to decrease the size of the rendered information. In accordance with systems and methods provided herein, moving from the distance b to the distance a invokes a rendered information-adjustment module that dynamically resizes, and, thereby, re-renders the originally rendered information on the display screen such that the re-rendered information is larger than the originally rendered information. Likewise, moving from the distance a to the distance b invokes the rendered information-adjustment module that dynamically resizes, and, thereby, re-renders the originally rendered information on the display screen such that the re-rendered information is smaller than the originally rendered information. Additionally or alternatively, the systems and methods provided herein are configured to account for a hyperopic user of the mobile computing device.

FIGS. 2A and 2B provide a schematic illustrating dynamically resizing rendered information on a display screen of a mobile computing device in accordance with some embodiments.

In accordance with systems and methods provided herein, moving a mobile computing device from a first distance (e.g., the distance a in FIG. 1A or FIG. 1E) to a second distance (e.g., the distance b in FIG. 1B or FIG. 1F) from a user of the mobile computing device invokes a rendered information-adjustment module that can dynamically resize, and, thereby, re-render originally rendered information on a display screen of the mobile computing device. The re-rendered information can be either larger or smaller than the originally rendered information in accordance with the user's viewing comfort, vision, or a combination thereof as described herein.

As shown in FIG. 2A, for example, the originally rendered information can be relatively small and include, but is not limited to, rendered text 210A in a workspace of a text editor and rendered text 220A of a title bar. The originally rendered information can also include UI elements including, but not limited to, edit menu icon 232A and overflow menu icon 234A. Subsequent to re-rendering and resizing the originally rendered information, the re-rendered information can be larger as shown in FIG. 2B by re-rendered text 210B in the workspace of the text editor, re-rendered text 220B of the title bar, the edit menu icon 232B, and the overflow menu icon 234B. Due to the larger size of the re-rendered text 210B over the originally rendered text 210A, a UI element such as scroll bar 240B can rendered to enable the user to view the entirety of the re-rendered text 210B.

As shown in FIG. 2B, for example, the originally rendered information can be relatively large and include, but is not limited to, rendered text 210B in the workspace of the text editor and rendered text 220B of the title bar. The originally rendered information can also include edit menu icon 232B and overflow menu icon 234B. Subsequent to re-rendering and resizing the originally rendered information, the re-rendered information can be smaller as shown in FIG. 2A by re-rendered text 210A in the workspace of the text editor, re-rendered text 220A of the title bar, the edit menu icon 232A, and the overflow menu icon 234A. Due to the smaller size of the re-rendered text 210A over the originally rendered text 210B, the scroll bar 240B does not need to be re-rendered for the user to view the entirety of the re-rendered text 210A.

It should be understood that while re-rendered text such as the re-rendered text 210B or 210A respectively appears larger or smaller to a viewer of the re-rendered text, the font size of the originally rendered text actually does not change. As such, whether the user prints, for example, the originally rendered text 210A or the re-rendered text 210B, the size of the text in the print remains constant.

FIGS. 3A and 3B provide a schematic illustrating dynamically resizing rendered information on a display screen of a personal computer in accordance with some embodiments.

While mobile computing devices have primarily been described to this point, it should be understood that systems provided herein also include electronic devices such as personal computers, televisions, smart bicycles, and smart automobiles so long as the electronic devices include at least one or more facial proximity sensors (e.g., cameras, infrared sensors, lasers, radio sensors, ultrasound sensors, etc. As such, when a user moves from a first distance (e.g., the distance a in FIG. 1A or FIG. 1E) to a second distance (e.g., the distance b in FIG. 1B or FIG. 1F) from an electronic device such as a personal computer, a rendered information-adjustment module that can dynamically resize, and, thereby, re-render originally rendered information on a display screen of a monitor of the personal computer. The re-rendered information can be either larger or smaller than the originally rendered information in accordance with the user's viewing comfort, vision, or a combination thereof as described herein.

As shown in FIG. 3A, for example, the originally information can be relatively small and include, but is not limited to, rendered text 310A in a workspace of a text editor (e.g., Notepad) and rendered text 320A of a title bar. The originally rendered information can also include UI elements including, but not limited to, window elements such as window minimize button 332A, window maximize button 334A, and window close button 336A. Subsequent to re-rendering and resizing the originally rendered information, the re-rendered information can be larger as shown in FIG. 3B by re-rendered text 310B in the workspace of the text editor, re-rendered text 320B of the title bar, the window minimize button 332B, the window maximize button 334B, and the window close button 336B. Due to the larger size of the re-rendered text 310B over the originally rendered text 310A, a UI element such as scroll bar 340B can rendered to enable the user to view the entirety of the re-rendered text 310B.

As shown in FIG. 3B, for example, the originally rendered information can be relatively large and include, but is not limited to, rendered text 310B in the workspace of the text editor and rendered text 320B of the title bar. The originally rendered information can also include window minimize button 332B, window maximize button 334B, and window close button 336B. Subsequent to re-rendering and resizing the originally rendered information, the re-rendered information can be smaller as shown in FIG. 3A by re-rendered text 310A in the workspace of the text editor, re-rendered text 320A of the title bar, the window minimize button 332A, the window maximize button 334A, and the window close button 336A. Due to the smaller size of the re-rendered text 310A over the originally rendered text 310B, the scroll bar 340B does not need to be re-rendered for the user to view the entirety of the re-rendered text 310A.

Again, it should be understood that while re-rendered text such as the re-rendered text 310B or 310A respectively appears larger or smaller to a viewer of the re-rendered text, the font size of the originally rendered text actually does not change. As such, whether the user prints, for example, the originally rendered text 310A or the re-rendered text 310B, the size of the text in the print remains constant.

FIG. 4 provides a schematic illustrating a rendered information-adjustment module 400 in accordance with some embodiments.

The rendered information-adjustment module 400 can reside in an electronic device such as a mobile computing device, a personal computer, a television, a smart bicycle, or a smart automobile, or in a portion of the electronic device such as a portion of the mobile computing device or a portion the personal computer, the television, the smart bicycle, or the smart automobile. One or more modules selected from vision properties module 410, user properties module 420, distance module 430, and display modification module 440 of the rendered information-adjustment module 400 can be implemented or executed using one or more hardware processors including processor 820 of FIG. 8. The rendered information-adjustment module 400 can be part of an operating system ("OS") including OS 834 of FIG. 8 or another software system (e.g., other software 836 of FIG. 8) of the electronic device.

The vision properties module 410 can be configured to receive an initial set of vision properties for the user through, for example, a graphical user interface ("GUI"). The vision properties can include the user's inter-eye or inter-pupillary distance; the user's visual acuity; whether or not the user uses or requires corrective lenses such as contact lenses, glasses, or both contact lenses and glasses; the user's corrective lens prescription (e.g., corrective lens prescription for myopia, hyperopia, hyperopia, astigmatism, etc.); and the like. The vision properties module 410 can also be configured to update the initial set of vision properties for the user on a periodic basis to provide a current set of vision properties. The periodic basis can very per defaults or user preferences. For example, many users that require corrective lenses visit their eye doctors on a yearly basis. As such, the vision properties module 410 can be configured with a default to update the initial set of vision properties for the user on a yearly basis to provide the current set of vision properties for the user. The vision properties module 410 can be configured to store the initial set or the current set of vision properties in a database as a vision record 415.

The vision properties module 410 can also be configured to automatically determine certain vision properties such as the user's inter-eye or inter-pupillary distance, as well as the user's vision state. The user's vision state can include whether or not the user is wearing glasses per the initial set or the current set of vision properties in the vision record 415. For example, to automatically determine the vision state of the user, the electronic device can capture an image of the user and use the image to identify glasses or another vision-correction device on the user. The rendered information-adjustment module 400 can re-render originally rendered information accordingly.

The user properties module 420 can be configured to receive an initial set of user properties such as user preferences through, for example, a GUI. The user preferences can include the user's preferences with respect to re-rendering frequency, subpixel rendering technology, brightness, contrast, color settings, and the like, which can directly affect readability of rendered information among different users having the same visual acuity. The user properties module 420 can be configured to store the user preferences in a database as a user preferences record 425. The user properties module 420 can be configured to update the initial set of user properties to provide a current set of user properties at any time through the GUI or in accordance with learned user behaviors from user behavior record 427.

The user properties module 420 can also be configured to learn user behaviors through direct observation (e.g., using a camera), user adjustments to the display or rendered information on the display, or a combination thereof. User behaviors can include the user's viewing habits such as the frequency with which the user moves while viewing, the extent to which the user moves while viewing, zooming behaviors, the most common viewing time of day, the amount of light in the user's viewing environment, and the like. The user properties module 420 can be configured to store the user behaviors in a database as the user behavior record 427. Once the user behaviors are learned, the rendered information-adjustment module 400 can provide a more comfortable and stable viewing experience for the user. For example, if the user preferences record 425 indicates the user prefers a low-frequency re-rendering frequency, and if the user often size-adjusts such as zooms in or zooms out (e.g., using shortcuts on one or more input devices such as keyboard CTRL key+mouse wheel scroll) to respectively increase or decrease text size per the user behavior record 427, the user properties module 420 can update the user's records and use the updated records to increase the re-rendering frequency for a more comfortable and stable viewing experience for the user.

The distance module 430 can be configured to determine a user's facial proximity to a display screen of an electronic device using one or more facial proximity sensors selected from any number of cameras, infrared sensors, radio sensors, and ultrasound sensors. For example, the mobile computing device 200A of FIG. 2A includes at least one camera 250A that can be used as a facial proximity sensor. To determine the user's facial proximity to the display screen of the electronic device, the distance module 430 can be configured to first determine distance data from facial proximity-sensor data provided by the one or more facial proximity sensors. Continuing with the camera example (e.g., the camera 250A of the mobile computing device 200A of FIG. 2A) of a facial proximity sensor, the distance module 430 can thus be configured to first determine distance data from one or images provided by the camera. The distance data can be determined (e.g., by trigonometric calculation) using a known inter-eye distance from the vision record 415 and a measured inter-eye distance from the one or more images. With the known distance data, the distance module 430 can be configured to subsequently determine the user's facial proximity, which can correspond directly to the distance data or be a derivative form thereof (e.g., a facial proximity factor) useful for one or more other modules.

The rendered information-adjustment module 400 can be configured with a facial proximity-sensor module (not shown in FIG. 4) to cooperate with the one or more facial proximity sensors for better facial proximity-sensor date. For example, the facial proximity-sensor module can be a camera module configured to suppress auto-correcting features when taking one or more images of the user with the camera. The auto-correcting features can include, but are not limited to, auto-correcting brightness and auto-correcting color balance. Suppression auto-correcting brightness and auto-correcting color balance, for example, maintains consistent brightness and color across one or more images for the distance module 430 to periodically determine the facial proximity of the user to the display screen.

Briefly, FIGS. 5, 6A, and 6B, will now be described, wherein: FIG. 5 provides a schematic illustrating user head motions accounted for by a rendered information-adjustment module in accordance with some embodiments; and wherein FIGS. 6A and 6B provide a schematic illustrating user head yaw and its effect on a raw measured inter-eye distance for the user in accordance with some embodiments.

While the distance data can be determined (e.g., by trigonometric calculation) using a known inter-eye distance from the vision record 415 and a measured inter-eye distance from the one or more images, the measured inter-eye distance from the one or more images can be affected by the user's head motions such as head pitch, head roll, and head yaw, which head motions are illustrated in FIG. 5 for user 599. Of the foregoing head motions, it should be appreciated that head yaw can have the greatest effect on the measured inter-eye distance from the one or more images. As shown in FIG. 6A, user 699A (or a schematic representation of eyes of the user 699A) can face the display without any appreciable head yaw, and the measured inter-eye distance without head yaw can be measured as $d_m$. However, as shown in FIG. 6B, user 699B (or a schematic representation of eyes of the user 699B) can obliquely face the display with a certain degree of head yaw, and the measured inter-eye distance with head yaw can be measured as $d_{m'}$. In the event that the user 699A and the user 699B are the same user, the measured inter-eye distance with head yaw $d_{m'}$ can be less than the measured inter-eye distance without head yaw $d_m$. To account for the discrepancy in the measured inter-eye distances $d_m$ and $d_{m'}$, other factors can be taken into consideration to account for the user's head yaw for accordingly adjusting (e.g., averaging) the measured inter-eye distance for dynamically resizing rendered information on the display screen. Other factors can include, for example, lighting changes on the user's face or a length of the user's nose, which can indicate the degree of head yaw.

Adverting to FIG. 4 and the distance module 430, instead of the at least one camera 250A of FIG. 2A, a number of cameras (e.g., a number of infrared cameras) in pairwise stereoscopic configurations can also be used to determine a user's facial proximity to the display screen of the electronic device. For example, at least one pair of cameras in a stereoscopic configuration can be set in the upper corners or the lower corners of a display device such as the upper corners or the lower corners of a mobile computing device. The cameras can each be configured to have the same resolution, and—if visible-light cameras—the resolution can be lower than the resolution of a conventional visible-light camera for a mobile computing device. In some embodiments, for example, the resolution can be selected from a resolution less than 12 megapixels ("MP"), 8 MP, 5 MP, 3 MP, and 2 MP. Such a low resolution can be achieved by skipping pixels or binning pixels in each camera of the number of cameras.

The distance module 430 can be configured to periodically determine a facial proximity to the display screen for the user in accordance with a periodic algorithm. The periodic algorithm is an important feature because in the case of battery-powered mobile computing devices, the periodic algorithm conserves the battery power by periodically invoking the one or more facial proximity sensors, which, in turn, reduces otherwise continuous battery power-draining size adjustments to the rendered information on the display screen. In some embodiments, periodicity for invoking the one or more facial proximity sensors by the periodic algorithm is adjusted in accordance with behavior intelligence provided by the user properties module 420 or the user behavior record 427.

The display modification module 440 can be configured to determine a direction and a magnitude for adjusting the rendered information on the display screen to a new size on the basis of the user's facial proximity to the display screen and the user's visual acuity as provided by the distance module 430 and the vision properties module 410, respectively. A compositor can be configured to cooperate with the display modification module 440 to scale the rendered information in accordance with the direction and the magnitude determined by the display modification module 440. In a first example, according to the vision properties module 410, the user might be myopic or nearsighted, and according to the distance module 430, the user might be close (small facial proximity) to the display. In this first example, the display modification module 440 would determine the user would likely benefit from smaller rendered information. As such, the display modification module 440 would cooperate with the display interface 890 of FIG. 8 to adjust the rendered information in an adjustment in that direction. The magnitude of the adjustment would be in accordance with the user's visual acuity per the vision properties module 410. Likewise, in a second example, according to the vision properties module 410, the user might be myopic or nearsighted, and according to the distance module 430, the user might be far (large facial proximity) to the display. In this second example, the display modification module 440 would determine the user would likely benefit from larger rendered information. As such, the display modification module 440 would cooperate with the display interface 890 of FIG. 8 to adjust the rendered information in an adjustment in that direction. Again, the magnitude of the adjustment would be in accordance with the user's visual acuity per the vision properties module 410. Likewise, in a third example, according to the vision properties module 410, the user might be hyperopic or farsighted, and according to the distance module 430, the user might be close (small facial proximity) to the display. In this third example, the display modification module 440 would determine the user would likely benefit from larger rendered information. As such, the display modification module 440 would cooperate with the display interface 890 of FIG. 8 to adjust the rendered information in an adjustment in that direction. Again, the magnitude of the adjustment would be in accordance with the user's visual acuity per the vision properties module 410. Likewise, in a fourth example, according to the vision properties module 410, the user might be hyperopic or farsighted, and according to the distance module 430, the user might be far (large facial proximity) to the display. In this fourth example, the display modification module 440 would determine the user would likely benefit from smaller rendered information. As such, the display modification module 440 would cooperate with the display interface 890 of FIG. 8 to adjust the rendered information in an adjustment in that direction. Again, the magnitude of the adjustment would be in accordance with the user's visual acuity per the vision properties module 410.

In view of the foregoing, in some embodiments systems and methods include the following:

The rendered information includes, for example, rendered information selected from i) rendered text, ii) rendered images, iii) rendered icons, and iv) rendered windows presented on the display screen. The entire image and all the text on all of the displayed screen can be altered in size based on a distance of a user to that display screen as well as factoring in any vision correction known for the user based on a user profile maintained for that user. Another way of saying this is dynamically changing the density (dots per inch ["DPI"]) of the display screen.

Dynamically changing the size of the rendered information, including images and text, on the entire display screen makes for easier user convenience and a better user experience with the mobile device. Also, the new concept will not consume as much power as other methods out there.

A first main embodiment calculates a distance to a user from the display screen of a mobile device based on the measured distance between the eyes of the user and the portion of the screen that this measured distance takes up on the screen. The bigger the measured distance between the user's eyes, the closer the user is to the screen. A reference chart of measured between the user's eyes to equivalent distance of user relative to display screen may be used/referenced and/or an algorithm that performs some trigonometry calculations can be used to determine the distance of the user relative to the screen. Note, a small variance exists between the distance between the eyes of people, which is smaller than the differences in the width of a human face across the different human races and sizes of humans.

The distance to the user's face may be calculated using a "field of view"-estimate, and some assumptions about the average distance between the eyes of a person's face. The field of view is determined by the percent the face takes up relative to known actual size of the display screen. The system can calculate the distance of the head from the camera by way of trigonometry. At this point we have the position of the head in relation to the camera.

The rendered information-adjustment module dynamically changes rendered text size based on a user's distance from the screen. The system will track the distance between a user's eyes and adjust the rendered text size and size of window of an image to an optimal size based on how far away the user is relative to the display screen.

Implementation of distance tracking consists of four main parts: 1) one or more cameras; 2) a face detector application; 3) a tracking mechanism; and 4) a rendered information-adjustment module to change the rendered text and image size.

A first embodiment that measures the distance to the user in order to auto adjust text and image sizes is exclusive to mobile devices as opposed to bigger size screens of televisions; and thus, does not need to factor in head angle offset. Most of the time a person using a mobile device will look straight into the smaller display screens of a mobile device and not have their head at an angle relative to the display screen of the mobile device. With larger display screens this may not be true, and typically with screens the size of a television, almost all the time, multiple users will have their heads at various angles with respect to being at a perpendicular angle to the display screen. The head angle offset will affect the measured distance between the user's eyes and its relative proportional measured size relative to the size of the display screen.

By using the measurement of the distance between the eyes of the user to determine how far away user is relative to the display screen, this creates several benefits. Low lighting and other lighting effect issues are now minimized because of the whites of human eyes being easy to detect compared to different tones of skin color across the spectrum of human races and the edge of their faces corresponding. Functionally, the design allows changing the rendered text size and image size in the dark based on measuring the whites of the eyes of the user and the whites reflecting the light of the screen.

Again, a smaller deviation exists across the diversity of human races with respect to the distance between their eyes as opposed to the width of the entire faces.

The concepts eliminate lighting condition problems and skin tone problems associated with humans by measuring the width of a face by instead measuring a distance between the whites of human's eyes.

The current design also incorporates vision correction of the user to be factored into determining a size of the image and/or text rendered on the display screen.

The concept dynamically changes the rendered screen density depending on the vision correction known about the user and distance of the users face or eyes from the display screen. The vision correction on about the user is retrieved from the user's profile as well as potentially determining whether the user is currently wearing reading glasses or not.

The vision properties module user interface will solicit the prescription value of the users glasses/DP value of the user and their eyes.

The algorithm may take into factor in vision correction of the user. A user may be farsighted and thus need to have the rendered images and text size made bigger the closer the user is to the display screen. Likewise, the adaptive algorithm will take into account if the user is nearsighted; and thus, the adaptive algorithm needs to make the text size bigger the farther that the user is away from the display screen.

Using a camera with a low power consumption typically helps because these low power cameras do not change the focus or the size of the aperture of the camera very much as most of the face is always in focus compared to a more expensive camera that can vary the aperture. For mobile devices with the more expensive cameras, the rendered information-adjustment module can make the face of the user in focus and then allow a distance calculation to be made but not before the camera autofocus is complete on the image of the user.

The rendered information-adjustment module uses a self-correcting algorithm that adapts how often the measurement is made to determine distance of the user relative to this user's behavior based on track motion behavior of the user. This is all in an attempt to make the screen size of the rendered text or images in the window stay relatively constant once they have been initially changed in size and then have slower transitions in changing the rendered text size after the initial setting of the rendered text size. This is so that the rendered text size and images are not frequently changing on the user, which can disorientate/annoy the user even when they're just sitting looking at the screen but moving back-and-forth in place quite a bit. Some users tend to move quite a bit while looking at a display screen where as other users tend to remain relatively motionless when looking at a display screen. The system attempts to fix problems of popular desk activities like slouching and drinking coffee while looking at the display screen. The system attempts to fix problems, such as the rendered text size changing frequently and bouncing around a lot due to minor user movements and/or side effects of a camera auto focusing and changing the brightness or color of an in-focus image.

The rendered information-adjustment module uses a periodic algorithm to ensure that the one or more cameras are not kept on all the time to make a face measurement. Rather the cameras periodically turned on to make the face measurement to track the distance between the user relative to the screen which saves power consumption in the device and also reduces that frequency that the rendered text size will change on the display screen. How often the one or more cameras are turned on is based on a standard threshold amount modified by the actual behavior of this user has track by a user profile of this user. The self-regulating algorithm determines the frequency to check the distance between the user and then resize the rendered text and image sizes based on date in the user profile of how often and the motion of this particular user when watching the screen.

An adaptive algorithm is used to dynamically change the rendered text size in unit sizes based on the relative distance of the user to the display screen.

The concept may determine the distance between the user's eyes and then take that measurement and through one or more trigonometry calculations determine what is the relative distance of the user to the display screen.

The concept will use a security camera image tracking algorithm which is not based on color histograms to track users but rather uses neural networks.

The first embodiment may get away with using one camera in the mobile device because it can all be based on just a 2-D measurement between the eyes of the user. A second embodiment, has multiple cameras in the mobile device that cooperate to get the depth perception of angles of the face, which gives three dimensional images and then determines head offset angle to factor into what the actual distance of the user is from the display screen with a head at an angle toward a large display screen such as a television screen.

The user profile will be based on who is logged into the mobile device when multiple users use the mobile device.

The algorithm can also factor in the actual size of the screen into how often distance checking must be made, smaller screen resizing is made less often, and then whether a head angle offset calculation needs to be factored in determining the distance between the user and the display screen.

Again, low-powered cameras can be used to determine the distance and then no need to worry about whether the user is in focus or not because merely all objects within 4-6 feet of the camera are in focus.

When a standard high-quality camera is used in a mobile device then power consumption is taken care of by turning on the camera only periodically to take distance measurement and sending a threshold to not turn on more than X amount, such as every five seconds, in order to not drain power from the mobile device.

The tracking algorithm locks onto the image of a user via using a neural network image tracker. Note, the facial recognition image need not be a high-powered or high calculation facial recognition algorithm. A low power consumption and fast-calculating facial recognition application can be used because merely the distance between users eyes needs to be accurately measured rather than accurately determining at least six points of distinction on the human face in order to properly match the identity of a human in face recognition to the captured image of the user.

Again, the rendered information-adjustment module increases or decreases the size of rendered text as well as optionally increases or decreases the window size showing an image.

In the flow path of block diagrams of modules, the rendered information-adjustment module with the algorithm to scale up or scale down the rendered text size and/or window size of an image may be before the decoder module or after the decoder module but before the display screen rendering module before putting the images and text on the display screen.

The information on whole screen is increased or decreased in size as opposed to a prior technique in which a small portion of the screen was magnified with a virtual magnifying glass.

The head-angle offset calculation is only factored in based on the size of the screen. For a small-sized display screen, such as on a mobile phone, iPod, etc., no head-angle offset calculation is necessary. On larger screen sizes such as televisions, however, a head offset measurement and subsequent calculation can be factored in. The head-angle offset calculation is because we want to counteract the distortion that arises when the user is looking at the screen from an angle. In the second embodiment, with multiple cameras the system can detect the face in all positions, for instance if the head was tilted, or turned slightly away.

Facial recognition software is based on the ability to recognize a face and then measure the various features of the face.

Every face has numerous, distinguishable landmarks, the different peaks and valleys that make up facial features including the distance between the eyes. The distance between the eyes are measured creating a numerical code, called a faceprint, representing the face in the database.

The concept uses face detection, in one embodiment, specifically the eyes, using camera and dynamically update screen dpi and rendered text size. A front-side camera can be used to detect a user's face—depending on how far the user's face is—and an estimated distance can be calculated to for subsequently dynamically changing screen and rendered text size. User input can be used as a secondary factor. For example, this works for 20/20 vision. If the person is farsighted and doesn't have reading glasses, the user can in put his or her farsightedness as user input.

Proximity sensor using radio waves such a sonar or radar may be used instead of a camera measuring the distance between the user and the screen. This proximity sensor may determine the distance of the users face to the screen, and then factor in the vision correction of the user in the user profile.

Network

FIG. 7 illustrates a number of electronic systems and devices communicating with each other in a network environment in accordance with some embodiments. The network environment 100 has a communications network 220. The network 220 can include one or more networks selected from an optical network, a cellular network, the Internet, a Local Area Network (LAN), a Wide Area Network (WAN), a satellite network, a fiber network, a cable network, and combinations thereof. In some embodiments, the communications network 220 is the Internet. As shown, there may be many server computing systems and many client computing systems connected to each other via the communications network 220. However, it should be appreciated that, for example, a single client computing system can also be connected to a single server computing system. As such, FIG. 7 illustrates any combination of server computing systems and client computing systems connected to each other via the communications network 220.

The communications network 220 can connect one or more server computing systems selected from at least a first server computing system 204A, a second server computing system 204B, and a third server computing system 204C to each other and to at least one or more client computing systems as well. The server computing systems 204A, 204B, and 204C can respectively optionally include organized data structures such as databases 206A, 206B, and 206C. Each of the one or more server computing systems can have one or more virtual server computing systems, and multiple virtual server computing systems can be implemented by design. Each of the one or more server computing systems can have one or more firewalls to protect data integrity.

The at least one or more client computing systems can be selected from a first mobile computing device 202A (e.g., smartphone with an Android-based operating system), a second mobile computing device 202E (e.g., smartphone with an iOS-based operating system), a first wearable electronic device 202C (e.g., a smartwatch), a first portable computer 202B (e.g., laptop computer), a second portable computer 202D (e.g., laptop computer), and a third mobile computing device or third portable computer 202F (e.g., tablet with an Android- or iOS-based operating system). Each of the one or more client computing systems can have one or more firewalls to protect data integrity.

It should be appreciated that the use of the terms "client computing system" and "server computing system" is intended to indicate the system that generally initiates a communication and the system that generally responds to the communication. For example, a client computing system can generally initiate a communication and a server computing system generally responds to the communication. No hierarchy is implied unless explicitly stated. Both functions can be in a single communicating system or device, in which case, the client-server and server-client relationship can be viewed as peer-to-peer. Thus, if the first mobile computing device 202A (e.g., the client computing system) and the server computing system 204A can both initiate and respond to communications, their communications can be viewed as peer-to-peer. Likewise, communications between the one or more server computing systems (e.g., server computing systems 204A and 204B) and the one or more client computing systems (e.g., client computing systems 202A and 202C) can be viewed as peer-to-peer if each is capable of initiating and responding to communications. Additionally, the server computing systems 204A, 204B, and 204C include circuitry and software enabling communication with each other across the network 220.

Any one or more of the server computing systems can be a cloud provider. A cloud provider can install and operate application software in a cloud (e.g., the network 220 such as the Internet) and cloud users can access the application software from one or more of the client computing systems. Generally, cloud users that have a cloud-based site in the cloud cannot solely manage a cloud infrastructure or platform where the application software runs. Thus, the server computing systems and organized data structures thereof can be shared resources, where each cloud user is given a certain amount of dedicated use of the shared resources. Each cloud user's cloud-based site can be given a virtual amount of dedicated space and bandwidth in the cloud. Cloud applications can be different from other applications in their scalability, which can be achieved by cloning tasks onto multiple virtual machines at run-time to meet changing work demand. Load balancers distribute the work over the set of virtual machines. This process is transparent to the cloud user, who sees only a single access point.

Cloud-based remote access can be coded to utilize a protocol, such as Hypertext Transfer Protocol (HTTP), to engage in a request and response cycle with an application on a client computing system such as a mobile computing device application resident on the mobile computing device as well as a web-browser application resident on the mobile computing device. The cloud-based remote access can be accessed by a smartphone, a desktop computer, a tablet, or any other client computing systems, anytime and/or anywhere. The cloud-based remote access is coded to engage in 1) the request and response cycle from all web browser based applications, 2) SMS/twitter-based requests and responses message exchanges, 3) the request and response cycle from a dedicated on-line server, 4) the request and response cycle directly between a native mobile application resident on a client device and the cloud-based remote access to another client computing system, and 5) combinations of these.

In an embodiment, the server computing system 204A can include a server engine, a web page management component, a content management component, and a database management component. The server engine can perform basic processing and operating system level tasks. The web page management component can handle creation and display or routing of web pages or screens associated with receiving and providing digital content and digital advertisements. Users (e.g., cloud users) can access one or more of the server computing systems by means of a Uniform Resource Locator (URL) associated therewith. The content management component can handle most of the functions in the embodiments described herein. The database management component can include storage and retrieval tasks with respect to the database, queries to the database, and storage of data.

An embodiment of a server computing system to display information, such as a web page, etc. is discussed. An application including any program modules, apps, services, processes, and other similar software executable when executed on, for example, the server computing system 204A, causes the server computing system 204A to display windows and user interface screens on a portion of a media space, such as a web page. A user via a browser from, for example, the client computing system 202A, can interact with the web page, and then supply input to the query/fields and/or service presented by a user interface of the application. The web page can be served by a web server, for example, the server computing system 204A, on any Hypertext Markup Language (HTML) or Wireless Access Protocol (WAP) enabled client computing system (e.g., the client computing system 202A) or any equivalent thereof. For example, the client mobile computing system 202A may be a wearable electronic device, smartphone, a tablet, a laptop, a netbook, etc. The client computing system 202A can host a browser, a mobile application, and/or a specific application to interact with the server computing system 204A. Each application has a code scripted to perform the functions that the software component is coded to carry out such as presenting fields and icons to take details of desired information. Algorithms, routines, and engines within, for example, the server computing system 204A can take the information from the presenting fields and icons and put that information into an appropriate storage medium such as a database (e.g., database 206A). A comparison wizard can be scripted to refer to a database and make use of such data. The applications may be hosted on, for example, the server computing system 204A and served to the browser of, for example, the client computing system 202A. The applications then serve pages that allow entry of details and further pages that allow entry of more details.

Computing Systems

FIG. 8 illustrates a computing system that can be part of one or more of the computing devices in accordance with some embodiments. With reference to FIG. 8, components of the computing system 800 may include, but are not limited to, a processing unit 820 having one or more processing cores, a system memory 830, and a system bus 821 that couples various system components including the system memory 830 to the processing unit 820. The system bus 821 may be any of several types of bus structures selected from a memory bus or memory controller, a peripheral bus, and a local bus using any of a variety of bus architectures.

Computing system 800 typically includes a variety of computing machine-readable media. Computing machine-readable media can be any available media that can be accessed by computing system 800 and includes both volatile and nonvolatile media, and removable and non-removable media. By way of example, and not limitation, computing machine-readable media use includes storage of information, such as computer-readable instructions, data structures, other executable software or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by the computing device 800. Transitory media such as wireless channels are not included in the machine-readable media. Communication media typically embody computer readable instructions, data structures, other executable software, or other transport mechanism and includes any information delivery media. As an example, some client computing systems on the network 220 of FIG. 7 might not have optical or magnetic storage.

The system memory 830 includes computer storage media in the form of volatile and/or nonvolatile memory such as read only memory (ROM) 831 and random access memory (RAM) 832. A basic input/output system 833 (BIOS) containing the basic routines that help to transfer information between elements within the computing system 800, such as during start-up, is typically stored in ROM 831. RAM 832 typically contains data and/or software that are immediately accessible to and/or presently being operated on by the processing unit 820. By way of example, and not limitation, FIG. 8 illustrates that RAM 832 can include a portion of the operating system 834, application programs 835, other executable software 836, and program data 837.

The computing system 800 can also include other removable/non-removable volatile/nonvolatile computer storage media. By way of example only, FIG. 8 illustrates a solid-state memory 841. Other removable/non-removable, volatile/nonvolatile computer storage media that can be used in the example operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850.

The drives and their associated computer storage media discussed above and illustrated in FIG. 8, provide storage of computer readable instructions, data structures, other executable software and other data for the computing system 800. In FIG. 8, for example, the solid state memory 841 is illustrated for storing operating system 844, application programs 845, other executable software 846, and program data 847. Note that these components can either be the same as or different from operating system 834, application programs 835, other executable software 836, and program data 837. Operating system 844, application programs 845, other executable software 846, and program data 847 are given different numbers here to illustrate that, at a minimum, they are different copies.

A user may enter commands and information into the computing system 800 through input devices such as a keyboard, touchscreen, or software or hardware input buttons 862 (e.g., buttons on a remote control device), a microphone 863, a pointing device and/or scrolling input component, such as a mouse, trackball or touch pad. The microphone 863 can cooperate with speech recognition software. These and other input devices are often connected to the processing unit 820 through a user input interface 860 that is coupled to the system bus 821, but can be connected by other interface and bus structures, such as a parallel port, game port, or a universal serial bus (USB). A display monitor 891 or other type of display screen device is also connected to the system bus 821 via an interface, such as a display interface 890. In addition to the monitor 891, computing devices may also include other peripheral output devices such as speakers 897, a vibrator 899, and other output devices, which may be connected through an output peripheral interface 895.

The computing system 800 can operate in a networked environment using logical connections to one or more remote computers/client devices, such as a remote computing system 880. The remote computing system 880 can a personal computer, a hand-held device, a server, a router, a network PC, a peer device or other common network node, and typically includes many or all of the elements described above relative to the computing system 800. The logical connections depicted in FIG. 8 can include a personal area network (PAN) 872 (e.g., Bluetooth®), a local area network (LAN) 871 (e.g., Wi-Fi), and a wide area network (WAN) 873 (e.g., cellular network), but may also include other networks such as a personal area network (e.g., Bluetooth®). Such networking environments are commonplace in offices, enterprise-wide computer networks, intranets and the Internet. A browser application may be resident on the computing device and stored in the memory.

When used in a LAN networking environment, the computing system 800 is connected to the LAN 871 through a network interface or adapter 870, which can be, for example, a Bluetooth® or Wi-Fi adapter. When used in a WAN networking environment (e.g., Internet), the computing system 800 typically includes some means for establishing communications over the WAN 873. With respect to mobile telecommunication technologies, for example, a radio interface, which can be internal or external, can be connected to the system bus 821 via the network interface 870, or other appropriate mechanism. In a networked environment, other software depicted relative to the computing system 800, or portions thereof, may be stored in the remote memory storage device. By way of example, and not limitation, FIG. 8 illustrates remote application programs 885 as residing on remote computing device 880. It will be appreciated that the network connections shown are examples and other means of establishing a communications link between the computing devices may be used.

As discussed, the computing system 800 can include a processor 820, a memory (e.g., ROM 831, RAM 832, etc.), a built in battery to power the computing device, an AC power input to charge the battery, a display screen, a built-in Wi-Fi circuitry to wirelessly communicate with a remote computing device connected to network.

It should be noted that the present design can be carried out on a computing system such as that described with respect to FIG. 8. However, the present design can be carried out on a server, a computing device devoted to message handling, or on a distributed system in which different portions of the present design are carried out on different parts of the distributed computing system.

Another device that may be coupled to bus 821 is a power supply such as a DC power supply (e.g., battery) or an AC adapter circuit. As discussed above, the DC power supply may be a battery, a fuel cell, or similar DC power source that needs to be recharged on a periodic basis. A wireless communication module can employ a Wireless Application Protocol to establish a wireless communication channel. The wireless communication module can implement a wireless networking standard.

In some embodiments, software used to facilitate algorithms discussed herein can be embodied onto a non-transitory machine-readable medium. A machine-readable medium includes any mechanism that stores information in a form readable by a machine (e.g., a computer). For example, a non-transitory machine-readable medium can include read only memory (ROM); random access memory (RAM); magnetic disk storage media; optical storage media; flash memory devices; Digital Versatile Disc (DVD's), EPROMs, EEPROMs, FLASH memory, magnetic or optical cards, or any type of media suitable for storing electronic instructions.

Note, an application described herein includes but is not limited to software applications, mobile apps, and programs that are part of an operating system application. Some portions of this description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms can be written in a number of different software programming languages such as C, C+, or other similar languages. Also, an algorithm can be implemented with lines of code in software, configured logic gates in software, or a combination of both. In an embodiment, the logic consists of electronic circuits that follow the rules of Boolean Logic, software that contain patterns of instructions, or any combination of both.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

Many functions performed by electronic hardware components can be duplicated by software emulation. Thus, a software program written to accomplish those same functions can emulate the functionality of the hardware components in input-output circuitry.

As such, provided herein in some embodiments is an apparatus comprising a rendered information-adjustment module of a mobile computing device, wherein the rendered information-adjustment module is configured to cooperate with components of the mobile computing device including one or more processors to execute instructions, one or more memories to store information, one or more data input components to receive data input from a user of the mobile computing device, a communication circuit to establish a communication link to communicate with other computing devices external to the mobile computing device, a display screen to display at least some of the information stored in the one or more memories, one or more facial proximity sensors configured to provide facial proximity-sensor data for the user, and a battery to provide battery power to the mobile computing device, wherein portions of the rendered information-adjustment module implemented in software are stored in the one or more memories and are executed by the one or more processors, wherein the rendered information-adjustment module is configured to cooperate with a display interface to dynamically size-adjust rendered information displayed on the display screen in cooperation with a distance module configured to periodically determine a facial proximity to the display screen for the user in accordance with a periodic algorithm, a vision properties module configured to collect vision properties and store the vision properties in a vision record for the user, and a display modification module configured to determine a direction and a magnitude for adjusting the rendered information to a new size, and wherein the periodic algorithm conserves the battery power by periodically invoking the one or more facial proximity sensors, which, in turn, reduces otherwise continuous battery power-draining size adjustments to the rendered information on the display screen. In some embodiments, the rendered information-adjustment module is configured to cooperate with the display interface to dynamically size-adjust rendered information displayed on the display screen in further cooperation with a user properties module configured to collect and store user behaviors including frequency of user movement in a user behavior record, wherein periodicity for invoking the one or more facial proximity sensors by the periodic algorithm is adjusted in accordance with behavior intelligence provided by the user properties module. In some embodiments, the vision properties include a corrective lens prescription for the user, the corrective lens prescription corresponds to a corrective lens prescription for myopia, hyperopia, presbyopia, or astigmatism, and the user behaviors include size adjustments to the rendered information manually made by the user. In some embodiments, the one or more facial proximity sensors are selected from any number of cameras, infrared sensors, radio sensors, and ultrasound sensors, and the distance module is configured to determine the facial proximity based upon distance data derived from facial proximity-sensor data provided by the one or more facial proximity sensors. In some embodiments, the one or more facial proximity sensors include a camera, the facial proximity-sensor data provided by the camera includes one or more images, and the distance data is derived from a known inter-eye distance for the user and a measured inter-eye distance for the user in the one or more images. In some embodiments, the measured inter-eye distance for the user in the one or more images compensates for any one or more head effects selected from head pitch, head roll, and head yaw. In some embodiments, the rendered information-adjustment module is configured to suppress auto-correcting features of the camera including auto-correcting brightness and auto-correcting color balance when taking the one or more images. In some embodiments, the one or more facial proximity sensors includes at least one pair of low-resolution cameras in a stereoscopic configuration, the facial proximity-sensor data provided by the at least one pair of low-resolution cameras includes one or more images, and the distance data is derived from a known inter-eye distance for the user and a measured inter-eye distance for the user in the one or more images. In some embodiments, each camera of the two or more cameras has a lower resolution than a conventional camera for a mobile computing device. In some embodiments, the lower resolution is selected from a resolution less than 12 megapixels ("MP"), 8 MP, 5 MP, 3 MP, and 2 MP, and skipping pixels or binning pixels in the two or more low-resolution cameras effects the lower resolution.

Also provided herein in some embodiments is a non-transitory machine-readable medium configured to store instructions and data that when executed by one or more processors on a mobile computing device, causes the mobile computing device to perform the following operations comprising re-rendering rendered information with a rendered information-adjustment module of the mobile computing device, wherein re-rendering the rendered information includes cooperating with components of the mobile computing device including one or more processors to execute instructions, one or more memories to store information, one or more data input components to receive data input from a user of the mobile computing device, a communication circuit to establish a communication link to communicate with other computing devices external to the mobile computing device, a display screen to display at least some of the information stored in the one or more memories, one or more facial proximity sensors configured to provide facial proximity-sensor data for the user, and a battery to provide battery power to the mobile computing device, wherein portions of the rendered information-adjustment module implemented in software are stored in the one or more memories and are executed by the one or more processors, and wherein re-rendering the rendered information further includes cooperating with a display interface and dynamically size-adjusting the rendered information displayed on the display screen; periodically determining with a distance module a facial proximity to the display screen for the user in accordance with a periodic algorithm; collecting vision properties with a vision properties module and storing the vision properties in a vision record for the user; determining with a display modification module a direction and a magnitude for adjusting the rendered information to a new size; and conserving the battery power by periodically invoking the one or more facial proximity sensors with the periodic algorithm, thereby reducing otherwise continuous battery power-draining size adjustments to the rendered information on the display screen. In some embodiments, the non-transitory machine-readable medium further comprises collecting and storing with a user properties module user behaviors including frequency of user movement in a user behavior record, wherein periodicity for invoking the one or more facial proximity sensors by the periodic algorithm is adjusted in accordance with behavior intelligence provided by the user properties module. In some embodiments, the vision properties include a corrective lens prescription for the user, size adjustments to the rendered information manually made by the user, or a combination thereof, and the corrective lens prescription corresponds to a corrective lens prescription for myopia, hyperopia, presbyopia, or astigmatism. In some embodiments, the non-transitory machine-readable medium further comprises determining with the distance module the facial proximity based upon distance data derived from facial proximity-sensor data provided by the one or more facial proximity sensors, wherein the one or more facial proximity sensors are selected from any number of cameras, infrared sensors, radio sensors, and ultrasound sensors. In some embodiments, the non-transitory machine-readable medium further comprises deriving the distance data from a known inter-eye distance for the user and a measured inter-eye distance for the user in one or more images, wherein the one or more facial proximity sensors includes a camera, and wherein the facial proximity-sensor data provided by the camera includes the one or more images. In some embodiments, the non-transitory machine-readable medium further comprises compensating for any one or more head effects selected from head pitch, head roll, and head yaw when determining the measured inter-eye distance for the user in the one or more images. In some embodiments, the non-transitory machine-readable medium further comprises suppressing auto-correcting features of the camera including auto-correcting brightness and auto-correcting color balance when taking the one or more images. In some embodiments, the non-transitory machine-readable medium further comprises deriving the distance data from a known inter-eye distance for the user and a measured inter-eye distance for the user in one or more images, wherein the one or more facial proximity sensors includes at least one pair of low-resolution cameras in a stereoscopic configuration, and wherein the facial proximity-sensor data provided by the at least one pair of low-resolution cameras includes the one or more images. In some embodiments, each camera of the two or more cameras has a lower resolution than a conventional camera for a mobile computing device. In some embodiments, the lower resolution is selected from a resolution less than 12 megapixels ("MP"), 8 MP, 5 MP, 3 MP, and 2 MP, and skipping pixels or binning pixels in the two or more low-resolution cameras effects the lower resolution.

While the foregoing design and embodiments thereof have been provided in considerable detail, it is not the intention of the applicant(s) for the design and embodiments provided herein to be limiting. Additional adaptations and/or modifications are possible, and, in broader aspects, these adaptations and/or modifications are also encompassed. Accordingly, departures may be made from the foregoing design and embodiments without departing from the scope afforded by the following claims, which scope is only limited by the claims when appropriately construed.

What is claimed is:

1. A non-transitory machine-readable medium configured to store instructions and data that when executed by one or more processors on an electronic device, causes the electronic device to perform the following operations, comprising:
re-rendering rendered information with a rendered information-adjustment module of the electronic device,
wherein re-rendering the rendered information includes cooperating with components of the electronic device including
one or more processors to execute instructions,
one or more memories to store information,
one or more data input components to receive data input from a user of the electronic device,
a communication circuit to establish a communication link to communicate with other electronic devices external to the electronic device,
a display screen to display at least some of the information stored in the one or more memories,
one or more facial proximity sensors configured to provide facial proximity-sensor data for the user, and
a battery to provide battery power to the electronic device, and
wherein re-rendering the rendered information further includes cooperating with a display interface and dynamically size-adjusting the rendered information displayed on the display screen;
periodically determining with a distance module a facial proximity to the display screen for the user in accordance with a periodic algorithm;
collecting vision properties with a vision properties module and storing the vision properties in a vision record for the user; and
determining with a display modification module a direction and a magnitude for adjusting the rendered information to a new size,
wherein the periodic algorithm conserves the battery power by periodically invoking the one or more facial proximity sensors, which, in turn, reduces otherwise continuous battery power-draining size adjustments to the rendered information on the display screen.

2. The non-transitory machine-readable medium of claim 1, further comprising:
collecting and storing with a user properties module user behaviors including frequency of user movement in a user behavior record,
wherein periodicity for invoking the one or more facial proximity sensors by the periodic algorithm is adjusted in accordance with behavior intelligence provided by the user properties module.

3. The non-transitory machine-readable medium of claim 1,
wherein the vision properties include a corrective lens prescription for the user, size adjustments to the rendered information manually made by the user, or a combination thereof, and
wherein the corrective lens prescription corresponds to a corrective lens prescription for myopia, hyperopia, presbyopia, or astigmatism.

4. The non-transitory machine-readable medium of claim 1, further comprising:
determining with the distance module the facial proximity based upon distance data derived from facial proximity-sensor data provided by the one or more facial proximity sensors,
wherein the one or more facial proximity sensors are selected from any number of cameras, infrared sensors, lasers, radio sensors, and ultrasound sensors.

5. The non-transitory machine-readable medium of claim 4, further comprising:
deriving the distance data from a known inter-eye distance for the user and a measured inter-eye distance for the user in one or more images,
wherein the one or more facial proximity sensors includes a camera, and
wherein the facial proximity-sensor data provided by the camera includes the one or more images.

6. The non-transitory machine-readable medium of claim 5, further comprising:
compensating for any one or more head effects selected from head pitch, head roll, and head yaw when determining the measured inter-eye distance for the user in the one or more images.

7. The non-transitory machine-readable medium of claim 5, further comprising:
suppressing auto-correcting features of the camera including auto-correcting brightness and auto-correcting color balance when taking the one or more images.

8. The non-transitory machine-readable medium of claim 4, further comprising:
deriving the distance data from a known inter-eye distance for the user and a measured inter-eye distance for the user in one or more images,
wherein the one or more facial proximity sensors includes at least one pair of cameras in a stereoscopic configuration, and
wherein the facial proximity-sensor data provided by the at least one pair of cameras includes the one or more images.

9. An apparatus, comprising:
a rendered information-adjustment module of an electronic device,
wherein the rendered information-adjustment module is configured to cooperate with components of the electronic device including
one or more processors to execute instructions,
one or more memories to store information,
one or more data input components to receive data input from a user of the electronic device,
a communication circuit to establish a communication link to communicate with other electronic devices external to the electronic device,
a display screen to display at least some of the information stored in the one or more memories,
one or more facial proximity sensors configured to provide facial proximity-sensor data for the user, and
a battery to provide battery power to the electronic device,
wherein portions of the rendered information-adjustment module implemented in software are stored in the one or more memories and are executed by the one or more processors,
wherein the rendered information-adjustment module is configured to cooperate with a display interface to dynamically size-adjust rendered information displayed on the display screen in cooperation with
a distance module configured to periodically determine a facial proximity to the display screen for the user in accordance with a periodic algorithm,
a vision properties module configured to collect vision properties and store the vision properties in a vision record of a user profile stored for the user in the one or more memories, and
a display modification module configured to determine a direction and a magnitude for adjusting the rendered information to a new size, and
wherein the periodic algorithm conserves the battery power by periodically invoking the one or more facial proximity sensors, which, in turn, reduces otherwise continuous battery power-draining size adjustments to the rendered information on the display screen.

10. The apparatus of claim 9,
wherein the rendered information-adjustment module is configured to cooperate with the display interface to dynamically size-adjust rendered information displayed on the display screen in further cooperation with
a user properties module configured to collect and store user behaviors including frequency of user movement in a user behavior record,
wherein periodicity for invoking the one or more facial proximity sensors by the periodic algorithm is adjusted in accordance with behavior intelligence provided by the user properties module, and
wherein the rendered information that can be dynamically size-adjusted on the display screen includes i) a rendered text size, ii) a rendered window size, iii) a rendered image size, or iii) a combination thereof.

11. The apparatus of claim 10,
wherein the vision properties stored in the vision record of the user profile stored for the user in the one or more memories include a corrective lens prescription for the user,
wherein any vision properties known for the user are stored in the vision record of the user profile stored for the user in the one or more memories,
wherein the corrective lens prescription corresponds to a corrective lens prescription for myopia or nearsightedness, hyperopia or farsightedness, presbyopia, or astigmatism,
wherein the rendered information-adjustment module is configured with an adaptive algorithm to dynamically size-adjust the rendered information larger the farther away the user is from the display screen when the user is nearsighted,
wherein the rendered information-adjustment module is further configured with the adaptive algorithm to dynamically size-adjust the rendered information smaller the farther away the user is from the display screen when the user is farsighted, and
wherein the user behaviors stored by the user properties module in the user behavior record include size adjustments to the rendered information manually made by the user.

12. The apparatus of claim 9,
wherein the one or more facial proximity sensors are selected from any number of cameras, infrared sensors, lasers, radio sensors, and ultrasound sensors, and
wherein the distance module is configured to determine the facial proximity based upon distance data derived from facial proximity-sensor data provided by the one or more facial proximity sensors.

13. The apparatus of claim 12,
wherein the one or more facial proximity sensors includes no more than a single camera among any other facial proximity sensors,
wherein the facial proximity-sensor data provided by the camera includes one or more images, and
wherein the distance data derived from the facial proximity-sensor data by the distance module is derived from a known inter-eye distance for the user and a measured inter-eye distance for the user in the one or more images.

14. The apparatus of claim 9,
wherein the one or more facial proximity sensors include two or more cameras,
wherein a measured inter-eye distance for the user in one or more images compensates for any one or more head effects selected from the group consisting of head pitch, head roll, and head yaw based on the one or more images from the two or more cameras, and
wherein the distance module is configured to determine the facial proximity of the user to the display screen using one or more of the following methods selected from the group consisting of
1) referencing a reference chart of measured inter-eye distances for the user at different distances from the two or more cameras,
2) using an algorithm configured to perform trigonometric calculations to determine the facial proximity of the user to the two or more cameras, and
3) combinations thereof.

15. The apparatus of claim 9,
wherein the one or more facial proximity sensors includes a camera,
wherein the rendered information-adjustment module is configured to suppress auto-correcting features when taking one or more images of the user with the camera,
wherein the auto-correcting features include auto-correcting brightness and auto-correcting color balance, suppression of which maintains consistent brightness and color across the one or more images for the distance module to periodically determine the facial proximity of the user to the display screen.

16. The apparatus of claim 12,
wherein the one or more facial proximity sensors includes at least one pair of cameras in a stereoscopic configuration,
wherein the facial proximity-sensor data provided by the at least one pair of cameras includes one or more images, and
wherein the distance data is derived from a known inter-eye distance for the user and a measured inter-eye distance for the user in the one or more images.

17. The apparatus of claim 9,
wherein the periodic algorithm is configured to put in fixed delay periods of time between sampling measurements of the periodically determined facial proximity determined by the distance module based on motion behavior known about the user stored in the user profile in the one or more memories in an attempt to make a rendered size of text or images in a window stay relatively constant once they have been initially dynamically size-adjusted by the distance module.

18. The apparatus of claim 9,
wherein the electronic device is an electronic device selected from a mobile computing device, a smart bicycle, and a smart automobile.

19. An apparatus, comprising:
a rendered information-adjustment module of a television,
  wherein the rendered information-adjustment module is configured to cooperate with components of the television including
    one or more processors to execute instructions,
    one or more memories to store information,
    one or more data input components to receive data input from a user of the television,
    a communication circuit to establish a communication link to communicate with other electronic devices external to the television,
    a display screen to display at least some of the information stored in the one or more memories, and
    one or more facial proximity sensors configured to provide facial proximity-sensor data for the user,
  wherein portions of the rendered information-adjustment module implemented in software are stored in the one or more memories and are executed by the one or more processors,
  wherein the rendered information-adjustment module is configured to cooperate with a compositor and a display interface to dynamically size-adjust rendered information displayed on the display screen in cooperation with
    a distance module configured to periodically determine a facial proximity to the display screen for the user in accordance with a periodic algorithm,
    a vision properties module configured to collect vision properties and store the vision properties in a vision record of a user profile stored for the user in the one or more memories, and
    a display modification module configured to determine a direction and a magnitude for adjusting the rendered information to a new size
      wherein the periodic algorithm conserves the battery power by periodically invoking the one or more facial proximity sensors, which, in turn, reduces otherwise continuous battery power-draining size adjustments to the rendered information on the display screen.

20. The apparatus of claim 19,
wherein the compositor scales the rendered information in accordance with the direction and the magnitude determined by the display modification module.

* * * * *